United States Patent
Akama et al.

(10) Patent No.: US 6,613,774 B1
(45) Date of Patent: *Sep. 2, 2003

(54) PYRROLO [4,3,2-DE] QUINOLINE DERIVATIVES

(75) Inventors: Tsutomu Akama, Redwood City, CA (US); Hiroyuki Nagata, Shizuoka (JP); Atsuhiro Hasegawa, Tokyo (JP); Harumi Ue, Kanagawa (JP); Isami Takahashi, Tokyo (JP); Yutaka Saitoh, Shizuoka (JP); Kenichi Mochida, Kanagawa (JP); Shun-ichi Ikeda, Osaka (JP); Yutaka Kanda, Tokyo (JP)

(73) Assignee: Kyowa Hakko Kogyo Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/720,900

(22) PCT Filed: Jul. 8, 1999

(86) PCT No.: PCT/JP99/03691

§ 371 (c)(1),
(2), (4) Date: Jan. 2, 2001

(87) PCT Pub. No.: WO00/02879

PCT Pub. Date: Jan. 20, 2000

(30) Foreign Application Priority Data

Jul. 10, 1998 (JP) .......................... 10-195754

(51) Int. Cl.[7] .................. A61K 31/4745; C07D 471/06; A61P 37/06
(52) U.S. Cl. ........................... 514/292; 546/84
(58) Field of Search ............................. 514/292; 546/84

(56) References Cited

U.S. PATENT DOCUMENTS

| | | | |
|---|---|---|---|
| 4,959,370 A | 9/1990 | Crews et al. | 514/280 |
| 5,028,613 A | 6/1991 | Sun et al. | 514/292 |
| 5,414,001 A | 5/1995 | Ireland et al. | 514/287 |
| 5,684,018 A | * 11/1997 | Alexander | 514/316 |
| 5,843,955 A | 12/1998 | Tamaoki et al. | 514/292 |

OTHER PUBLICATIONS

Sof'ina et al. National Cancer Institute Monograph 55. Dec. 1980. Experimental Evaluation of Antitumor Drugs in the USa and USSR and Clinical Correlations. NIH Publication No. 80–1933. pp. 76–78.*
Calbiochem Signal Transduction Catalog & Technical Resource. 2001. p. 454.*
Schultz, et al., "In Vitro and in Vivo Antitumor Activity of the Phosphatidylinositol–3–kinase . . . ", Anticancer Research, vol. 15 (1995), pp. 1135–1140.
Tetrahedron Letters, vol. 31, No. 23 (1990), pp. 3271–3274.
The Journal of Antibiotics, vol. 50, No. 7 (1997), pp. 537–542.
The Journal of Antibiotics, vol. 50, No. 7 (1997), pp. 543–545.

* cited by examiner

Primary Examiner—Evelyn Mei Huang
(74) Attorney, Agent, or Firm—Fitzpatrick, Cella, Harper & Scinto

(57) ABSTRACT

LK6-A derivatives which have immmunosuppressive activity, cell growth inhibitory activity, anti-tumor activity, etc. and which are represented by general formula (I):

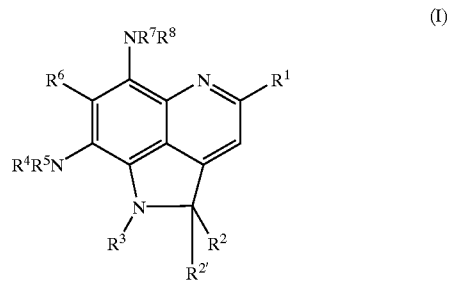

as defined herein, and pharmaceutically acceptable salts thereof.

18 Claims, No Drawings

PYRROLO [4,3,2-DE] QUINOLINE DERIVATIVES

This application is a 371 of PCT/JP99/03691, filed on Jul. 8, 1999.

TECHNICAL FIELD

The present invention relates to LK6-A derivatives which have immmunosuppressive activity, cell growth inhibitory activity, anti-tumor activity, etc., and pharmaceutically acceptable salts thereof.

BACKGROUND ART

Cyclosporin A [Nature, Vol. 280, p. 148 (1978)], FK506 [Immunol. Today, Vol. 10, p. 6 (1989)], mizoribine [Transplantation Proceed., Vol. 11, p. 865, (1979)], azathioprine [New Eng. J. Med., Vol. 268, p. 1315 (1963)], 15-deoxyspergualin [Transplantation Proceed., Vol. 22, p. 1606 (1990)], etc., which are known as low-molecular immunosuppressive agents, are used as therapeutic agents for autoimmune diseases, allergic diseases, infections caused by organ transplantation, etc. or as rejection inhibitors in organ transplantation. However, they are not entirely satisfactory in respect of efficacy, side effect, etc.

Plakinidines [Tetrahedron Lett., Vol. 31, p. 3271 (1990)] are reported as compounds having the pyrrolo[4, 3, 2-de] quinoline skeleton, but their immunosuppressive activity has not been known. As the pyrrolo[4, 3, 2-de]quinoline compound having immunosuppressive activity, LK6-A represented by the following formula (Japanese Published Unexamined Patent Application No. 151185/97) has been reported.

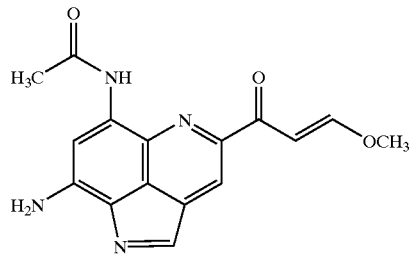

DISCLOSURE OF THE INVENTION

An object of the present invention is to provide novel LK6-A derivatives having excellent immunosuppressive activity, cell growth inhibitory activity, anti-tumor activity, etc. which are useful as therapeutic agents for autoimmune diseases, allergic diseases, and diseases caused by abnormal cell growth such as leukemia and cancers, or as rejection inhibitors in organ transplantation.

The present invention relates to LK6-A derivatives represented by general formula (I):

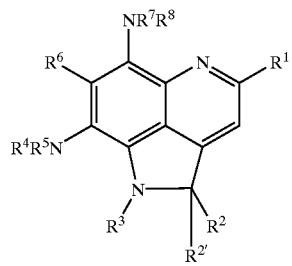

[wherein $R^1$ represents lower alkyl (the lower alkyl may be substituted by one to a substitutable number of, preferably 1–4 substituents which are the same or different and are selected from the group consisting of lower alkyl, hydroxy, lower alkoxy and halogen), lower alkanoyl (the lower alkyl moiety of the lower alkanoyl may be substituted by one to a substitutable number of, preferably 1–4 substituents which are the same or different and are selected from the group consisting of lower alkyl, hydroxy, lower alkoxy and halogen), carboxy, lower alkoxycarbonyl,

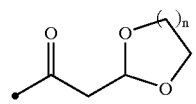

(wherein n represents 1 or 2) or COCH=CHR$^9$ {wherein $R^9$ represents substituted or unsubstituted lower alkoxy, substituted or unsubstituted aryl, substituted or unsubstituted heteroaryl or NR$^{10}$R$^{11}$ (wherein $R^{10}$ and $R^{11}$, which may be the same or different, each represents hydrogen, substituted or unsubstituted lower alkyl, substituted or unsubstituted lower alkenyl, substituted or unsubstituted lower alkynyl, substituted or unsubstituted aralkyl, substituted or unsubstituted aryl, substituted or unsubstituted heteroaryl, substituted or unsubstituted heteroaryl-substituted lower alkyl, substituted or unsubstituted tetrahydropyranyl, or substituted or unsubstituted tetrahydropyranylmethyl, or $R^{10}$ and $R^{11}$ are combined together with the adjoining N to form a substituted or unsubstituted heterocyclic group)};
$R^2$ represents hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted lower alkanoyl, substituted or unsubstituted lower alkanoyloxy; halogen, SR$^{12}$ (wherein $R^{12}$ represents substituted or unsubstituted lower alkyl, substituted or unsubstituted aryl, substituted or unsubstituted heteroaryl, substituted or unsubstituted aralkyl, substituted or unsubstituted heteroaryl-substituted lower alkyl, substituted or unsubstituted tetrahydropyranyl, or substituted or unsubstituted tetrahydropyranylmethyl), NR$^{13}$R$^{14}$ (wherein $R^{13}$ and $R^{14}$ have the same significances as the above $R^{10}$ and $R^{11}$, respectively) or azido;
$R^{2'}$ represents hydrogen or is combined with $R^3$ to represent a bond;
$R^3$ represents substituted or unsubstituted lower alkanoyl or is combined with $R^{2'}$ to represent a bond;
$R^4$ and $R^5$, which may be the same or different, each represents hydrogen, substituted or unsubstituted lower alkyl, substituted or unsubstituted lower alkanoyl, substituted or unsubstituted lower alkoxycarbonyl, substituted or unsubstituted aralkyloxycarbonyl, or substituted or unsubstituted heteroaryl-substituted lower alkoxycarbonyl;

$R^6$ represents hydrogen or halogen; and
$R^7$ and $R^8$, which may be the same or different, each represents hydrogen, substituted or unsubstituted lower alkyl, or substituted or unsubstituted lower alkanoyl;
provided that a compound wherein $R^1$ represents (E)-3-methoxyacryloyl, $R^2$, $R^4$, $R^5$ and $R^6$ represent hydrogen, $R^{2'}$ and $R^3$ are combined together to represent a bond, $R^7$ represents hydrogen and $R^8$ is acetyl is excluded], and pharmaceutically acceptable salts thereof.

Hereinafter, the compounds represented by general formula (I) are referred to as Compounds (I). The same shall apply to compounds of other formula numbers.

Preferred examples of the compounds of the present invention are shown in the following (a)–(h).

(a) Compound (I) in which $R^1$ represents $COCH=CHR^9$ (wherein $R^9$ has the same significance as defined above); $R^{2'}$ and $R^3$ are combined together to represent a bond; $R^4$, $R^5$ and $R^6$ represent hydrogen; and $R^7$ and $R^8$, which may be the same or different, each represents hydrogen or acetyl.

(b) Compound (I) in which $R^1$ represents lower alkyl (the lower alkyl may be substituted by one to a substitutable number of, preferably 1–4 substituents which are the same or different and are selected from the group consisting of lower alkyl, hydroxy, lower alkoxy and halogen) or lower alkanoyl (the lower alkyl moiety of the lower alkanoyl may be substituted by one to a substitutable number of, preferably 1–4 substituents which are the same or different and are selected from the group consisting of lower alkyl, hydroxy, lower alkoxy and halogen); $R^{2'}$ and $R^3$ are combined together to represent a bond; $R^4$, $R^5$ and $R^6$ represent hydrogen; and $R^7$ and $R^8$, which may be the same or different, each represents hydrogen or acetyl.

(c) Compound (I) in which $R^1$ represents:

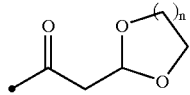

(wherein n has the same significance as defined above); $R^{2'}$ and $R^3$ are combined together to represent a bond; $R^2$, $R^4$, $R^5$ and $R^6$ represent hydrogen; and $R^7$ and $R^8$, which may be the same or different, each represents hydrogen or acetyl.

(d) Compound (I) in which $R^1$ represents (E)-3-methoxyacryloyl; $R^{2'}$ and $R^3$ are combined together to represent a bond; $R^4$ represents hydrogen; and $R^5$ represents substituted or unsubstituted lower alkoxycarbonyl or substituted or unsubstituted aralkyloxycarbonyl.

(e) Compound (I) in which $R^1$ represents $COCHR^{15}CH(OCH_3)_2$ (wherein $R^{15}$ represents hydrogen or lower alkyl); $R^{2'}$ and $R^3$ are combined together to represent a bond; $R^4$ and $R^5$, which may be the same or different, each represents hydrogen or lower alkyl; and $R^7$ and $R^8$, which may be the same or different, each represents hydrogen, substituted or unsubstituted lower alkyl or acetyl.

(f) Compound (I) in which $R^1$ represents $COCHR^{15a}CH(OCH_3)_2$ (wherein $R^{15a}$ represents hydrogen or halogen); $R^{2'}$ and $R^3$ are combined together to represent a bond; $R^4$ and $R^5$ represent hydrogen; and $R^7$, and $R^8$, which may be the same or different, each represents hydrogen or acetyl.

(g) Compound (I) in which $R^1$ represents 1-hydroxy-3-methoxypropyl; $R^{2'}$ and $R^3$ are combined together to represent a bond; $R^4$ and $R^5$ represent hydrogen; and $R^7$ and $R^8$, which may be the same or different, each represents hydrogen or acetyl.

(h) Compound (I) in which $R^2$ represents hydrogen or substituted or unsubstituted lower alkanoyloxy; $R^{2'}$ represents hydrogen; $R^3$ represents substituted or unsubstituted lower alkanoyl; $R^4$ represents hydrogen; $R^5$ represents substituted or unsubstituted lower alkanoyl; $R^7$ represents hydrogen; and $R^8$ represents acetyl.

Pharmaceutically acceptable salts of Compounds (I) shown in the above (a)–(h) are also one of the preferred embodiments of the present invention.

In the definitions of the groups in Compounds (I), the halogen means a fluorine, chlorine, bromine or iodine atom.

The lower alkyl includes straight-chain or branched alkyl groups having 1–9 carbon atoms, such as methyl, ethyl, propyl, isopropyl, butyl, isobutyl, pentyl, hexyl, heptyl, octyl and nonyl.

The lower alkyl moiety of the lower alkanoyl, the lower alkoxy, the lower alkoxycarbonyl and the lower alkanoyloxy has the same significance as the above lower alkyl, and the lower alkyl moiety of the heteroaryl-substituted lower alkyl and the heteroaryl-substituted lower alkoxycarbonyl represents a group in which one hydrogen atom is removed from the above lower alkyl.

The lower alkenyl includes alkenyl groups having 2–6 carbon atoms, such as vinyl, 1-propenyl, butenyl, pentenyl and hexenyl, and the lower alkynyl includes alkynyl groups having 2–6 carbon atoms, such as ethynyl, propynyl, butynyl, pentynyl and hexynyl.

The aryl includes aryl groups having 6–14 carbon atoms, such as phenyl, naphthyl and anthryl, and the heteroaryl includes 5- or 6-membered heteroaryl groups, such as pyridyl, furyl, thienyl, pyrrolyl, imidazolyl, pyrimidinyl, oxazolyl, thiazolyl, bicyclic heteroaryl group such as indolyl, benzofuryl, benzothienyl, quinolyl, quinazolinyl and quinoxalinyl. The heteroaryl moiety of the heteroaryl-substituted lower alkyl and the heteroaryl-substituted lower alkoxycarbonyl has the same significance as the above heteroaryl. The aryl moiety of the aralkyl and the aralkyloxycarbonyl has the same significance as the above aryl. The alkylene moiety of the aralkyl and the aralkyloxycarbonyl represents a group in which one hydrogen atom is removed from the above lower alkyl.

The heterocyclic group formed with the adjoining N includes pyrrolidinyl, piperidino, piperazinyl, morpholino, thiomorpholino, pyrrolyl, imidazolyl and pyrazolyl.

The substituted lower alkyl, the substituted lower alkoxy, the substituted lower alkenyl, the substituted lower alkynyl, the substituted lower alkanoyl, the substituted lower alkanoyloxy, the substituted lower alkoxycarbonyl, the substituted aralkyloxycarbonyl, the substituted aralkyl, the substituted heteroaryl-substituted-lower alkyl and the substituted heteroaryl-substituted lower alkoxycarbonyl each has one to a substitutable number of, preferably 1–5 substituents which are the same or different. Examples of the substituents include $NR^{16}R^{17}$ (wherein $R^{16}$ and $R^{17}$, which may be the same or different, each represents hydrogen or lower alkyl, or $R^{16}$ and $R^{17}$ are combined together with the adjoining N to form a heterocyclic group), hydroxy, lower alkoxy and lower alkanoyloxy. The lower alkyl, the heterocyclic group formed with the adjoining N, the lower alkoxy and the lower alkanoyloxy have the same significances as defined above, respectively.

The substituted aryl and the substituted heteroaryl each has 1–3 substituents which are the same or different. Examples of the substituents include lower alkyl, $NR^{16a}R^{17a}$ (wherein $R^{16a}$ and $R^{17a}$ have the same significances as the above $R^{16}$ and $R^{17}$, respectively), hydroxy, halogen, lower alkoxy, lower alkoxy-substituted lower alkoxy and lower alkanoyloxy. The lower alkyl, the lower alkoxy, the lower alkanoyloxy and the halogen have the same significances as defined above, respectively. The former lower alkoxy of the lower alkoxy-substituted lower alkoxy has the same significance as the above lower alkoxy, and the alkylene moiety of the latter lower alkoxy represents a group in which one hydrogen atom is removed from the above lower alkyl.

The substituted heterocyclic group formed with the adjoining N has 1–3 substituents which are the same or different. Examples of the substituents include hydroxy, lower alkyl, lower alkanoyl and arylcarbonyl. The lower alkyl and the lower alkanoyl have the same significances as defined above, respectively. The aryl moiety of the arylcarbonyl may be substituted by 1–3 functional groups arbitrarily selected from the group consisting of lower alkyl, lower alkanoyl, lower alkanoyloxy, hydroxy, lower alkoxy, amino, nitro, azido, carboxyl and lower alkoxycarbonyl. The alkyl moiety of the lower alkyl, lower alkanoyl, the lower alkanoyloxy, the lower alkoxy and the lower alkoxycarbonyl has the same significance as the above lower alkyl.

The substituted tetrahydropyranyl and the substituted tetrahydropyranylmethyl each has 1–4 substituents which are the same or different. Examples of the substituents include hydroxy, hydroxymethyl, lower alkoxy, lower alkoxymethyl, lower alkanoyloxy, lower alkanoyloxymethyl, benzyloxy, benzyloxymethyl and $NR^{18}R^{19}$ (wherein $R^{18}$ and $R^{19}$, which may be the same or different, each represents hydrogen, lower alkanoyl, lower alkoxycarbonyl, arylcarbonyl or aralkyloxycarbonyl). The lower alkyl moiety of the lower alkoxy, the lower alkoxymethyl, the lower alkanoyloxy, the lower alkanoyloxymethyl, the lower alkanoyl and the lower alkoxycarbonyl has the same significance as the above lower alkyl. The alkylene moiety of the aralkyloxycarbonyl has the same significance as the above alkylene moiety, and the aryl moiety of the arylcarbonyl and the aralkyloxycarbonyl has the same significance as the above aryl.

The pharmaceutically acceptable salts of Compounds (I) include acid addition salts, metal salts, ammonium salts, organic amine addition salts and amino acid addition salts. Examples of the acid addition salts are inorganic acid addition salts such as hydrochloride, hydrobromide, sulfate and phosphate, and organic acid addition salts such as formate, acetate, oxalate, benzoate, methanesulfonate, p-toluenesulfonate, maleate, malonate, fumarate, tartrate, citrate, succinate and lactate. Examples of the metal salts are alkali metal salts such as lithium salt, sodium salt and potassium salt, alkaline earth metal salts such as magnesium salt and calcium salt, aluminum salt and zinc salt. Examples of the ammonium salts are ammonium salt and tetramethylammonium salt. Examples of the organic amine addition salts are salts with morpholine and piperidine. Examples of the amino acid addition salts are salts with glycine, phenylalanine, aspartic acid, glutamic acid and lysine.

There may be various stereoisomers, regio isomers, geometrical isomers, tautomers, etc. for some of Compounds (I) of the present invention. The present invention encompasses all possible isomers and mixtures thereof in arbitrary mixture ratios.

The processes for preparing Compounds (I) are described below.

In the following processes, if the defined groups change under the conditions of the working method or are not appropriate for carrying out the method, the desired compounds can be obtained by using methods for introducing and eliminating protective groups which are conventionally used in synthetic organic chemistry [e.g., T. W. Greene, Protective Groups in Organic Synthesis, John Wiley & Sons Inc. (1981)]. If necessary, the order of the reaction steps such as introduction of a substituent may be changed.

Process 1

Compound (Ia), i.e., Compound (I) wherein $R^1$ represents acetyl; $R^2$, $R^4$, $R^5$, $R^6$, $R^7$ and $R^8$ represent hydrogen; and $R^{2'}$ and $R^3$ are combined together to represent a bond can be prepared according to the following reaction step.

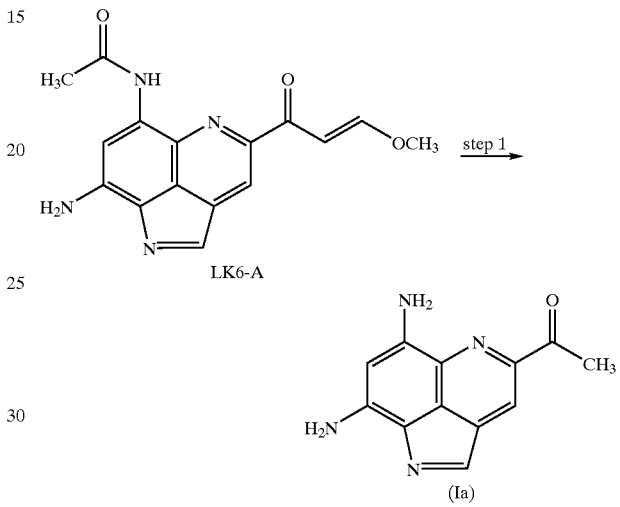

Step 1

Compound (Ia) can be obtained by treating LK6-A with an aqueous alkali solution in a solvent. Suitable solvents are water-miscible ones, for example, lower alcohols such as methanol and ethanol, tetrahydrofuran and dioxane, which may be used alone or as a mixture. As the aqueous alkali solution, 1–10 N aqueous solutions of alkalis such as sodium hydroxide and potassium hydroxide can be used. The reaction is carried out at a temperature between room temperature and the boiling point of the solvent used, preferably 50–100° C. for 0.5–10 hours.

The processes for preparing Compound (II), i.e., Compound (I) wherein $R^1$ represents $COCH=CHR^9$ (wherein $R^9$ has the same significance as defined above); $R^{2'}$ and $R^3$ are combined together to represent a bond; and $R^4$, $R^5$ and $R^6$ represent hydrogen are described in the following processes 2–7.

Process 2

Compound (IIa), i.e., Compound (I) wherein $R^2$, $R^4$, $R^5$ and $R^6$ represent hydrogen; $R^{2'}$ and $R^3$ are combined together to represent a bond; $R^1$ represents $COCH=CHNR^{10}R^{11}$ (wherein $R^{10}$ and R11 have the same significances as defined above); $R^7$ represents hydrogen; and $R^8$ represents acetyl can be prepared according to the following reactions step.

LK6-A $\xrightarrow{\text{step 2}}$ 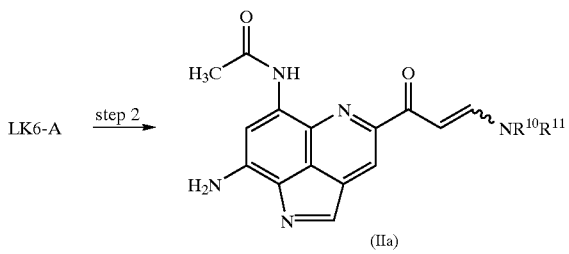

(In the formula, $R^{10}$ and $R^{11}$ have the same significances as defined above.)

Step 2

Compound (IIa) can be obtained by reaction of LK6-A with 1–20 equivalents of $HNR^{10}R^{11}$ (wherein $R^{10}$ and $R^{11}$ have the same significances as defined above) in an inert solvent. As the inert solvent, dimethyl sulfoxide, dimethylformamide, dimethylacetamide, tetrahydrofuran, etc. may be used. The reaction is carried out at 0–100° C., preferably 20–50° C. for 0.5–12 hours.

Process 3

Compound (IIb), i.e., Compound (I) wherein $R^1$ represents $COCH=CHNR^{10}R^{11}$ (wherein $R^{10}$ and $R^{11}$ have the same significances as defined above), $R^2$ represents $NR^{13}R^{14}$ (wherein $R^{13}$ and $R^{14}$ have the same significances as defined above, but $NR^{13}R^{14}$ here is the same as the above $NR^{10}R^{11}$); $R^4$, $R^5$ and $R^6$ represent hydrogen; $R^{2'}$ and $R^3$ are combined together to represent a bond; $R^7$ represents hydrogen; and $R^8$ represents acetyl can be prepared according to the following reaction step.

LK6-A $\xrightarrow{\text{step 3}}$ 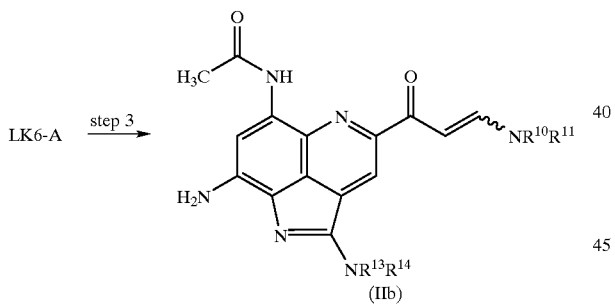

(In the formula, $R^{10}$, $R^{11}$, $R^{13}$ and $R^{14}$ have the same significances as defined above, and $NR^{13}R^{14}$ is the same as $NR^{10}R^{11}$.)

Step 3

Compound (IIb) can be obtained by reaction of LK6-A with 2–100 equivalents of $HNR^{10}R^{11}$ (wherein $R^{10}$ and $R^{11}$ have the same significances as defined above) under the conditions similar to those in step 2.

Process 4

Compound (IIc), i.e., Compound (I) wherein $R^1$ represents (E)-3-methoxyacryloyl; $R^2$ represents $SR^{12}$ (wherein $R^{12}$ has the same significance as defined above); $R^{2'}$ and $R^3$ are combined together to represent a bond; $R^4$, $R^5$ and $R^6$ represent hydrogen; $R^7$ represents hydrogen; and $R^8$ represents acetyl can be prepared according to the following reaction step.

LK6-A $\xrightarrow{\text{step 4}}$ 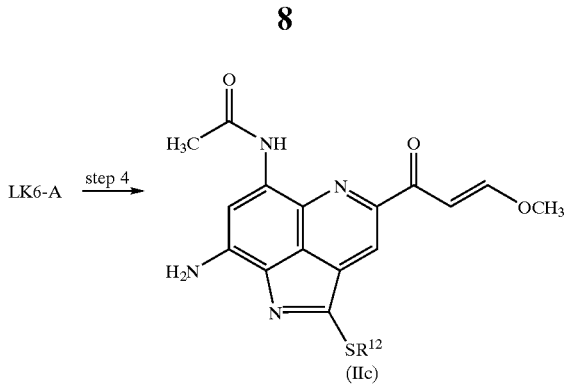

(In the formula, $R^{12}$ has the same significance as defined above.)

Step 4

Compound (IIc) can be obtained by reaction of LK6-A with 1–20 equivalents of $HSR^{12}$ (wherein $R^{12}$ has the same significance as defined above) in an inert solvent. The solvent, reaction temperature and reaction time are substantially the same as in the above step 2.

Process 5

Compound (IId), i.e., Compound (I) wherein $R^1$ represents (E)-3-methoxyacryloyl; $R^2$ represents halogen; $R^{2'}$ and $R^3$ are combined together to represent a bond; $R^4$, $R^5$ and $R^6$ represent hydrogen; $R^7$ represents hydrogen; and $R^8$ represents acetyl can be prepared according to the following reaction step.

LK6-A $\xrightarrow{\text{step 5}}$ 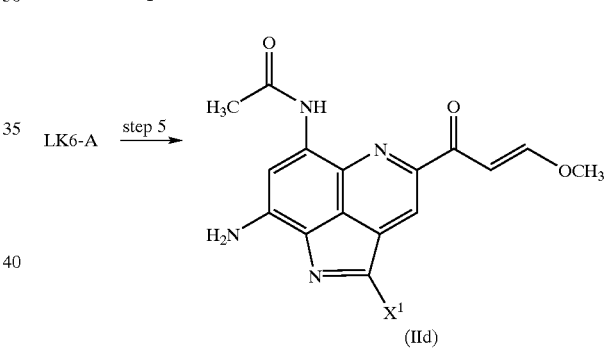

(In the formula, $X^1$ represents halogen.)

The halogen represented by $X^1$ has the same significance as the above halogen.

Step 5

Compound (IId) can be obtained by reaction of LK6-A with 1–20 equivalents of a halogenating reagent in an inert solvent.

As the inert solvent, halogen solvents such as dichloromethane, chloroform and carbon tetrachloride, ethers such as tetrahydrofuran and dioxane, lower alcohols such as methanol and ethanol, ethyl acetate, dimethylformamide, etc. may be used alone or as a mixture.

Examples of the halogenating reagent include bromine, chlorine, iodine, N-chlorosuccinimide, N-bromosuccinimide, N-iodosuccinimide, tetrabutylammonium tribromide and pyrrolidone hydrotribromide. The reaction is carried out at a temperature between −20° C. and the boiling point of the solvent used, preferably between 0° C. and room temperature for 0.1–12 hours.

Process 6

Compound (IIe), i.e., Compound (I) wherein $R^1$ represents (E)-3-methoxyacryloyl; $R^2$ represents hydrogen, halogen, $SR^{12}$ (wherein $R^{12}$ has the same significance as defined above) or $NR^{13}R^{14}$ (wherein $R^{13}$ and $R^{14}$ have the same significances as defined above); $R^{2'}$ and $R^3$ are combined together to represent a bond; $R^4$, $R^5$ and $R^6$ represent hydrogen; $R^7$ represents hydrogen; and $R^8$ represents acetyl can be prepared according to the following reaction step.

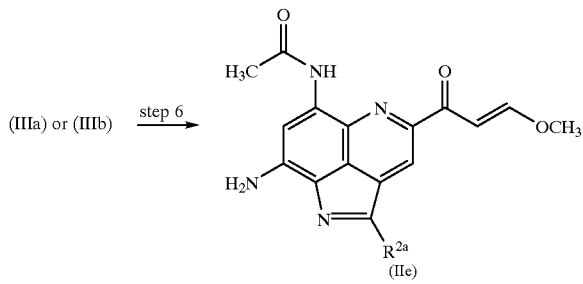

{In the formula, $R^{2a}$ represents hydrogen, halogen, $SR^{12}$ (wherein $R^{12}$ has the same significance as defined above) or $NR^{13}R^{14}$ (wherein $R^{13}$ and $R^{14}$ have the same significances as defined above).}

The halogen represented by $R^{2a}$ has the same significance as the above halogen.

Step 6

Compound (IIe) can be obtained by heating Compound (IIIa) or (IIIb) obtained in the following process 8 or 9 in an inert solvent, if necessary, in the presence of molecular sieves. As the inert solvent, dimethyl sulfoxide, dimethylformamide, etc. may be used. The reaction is carried out at a temperature between 50° C. and the boiling point of the solvent used, preferably 90–100° C. for 1–120 hours.

Process 7

Compound (IIf), i.e., Compound (I) wherein $R^1$ represents (E)-COCH=CHAr (wherein Ar represents substituted or unsubstituted aryl or substituted or unsubstituted heteroaryl which has the same significance as defined above); $R^2$, $R^4$, $R^5$, $R^6$, $R^7$ and $R^8$ represent hydrogen; and $R^{2'}$ and $R^3$ are combined together to represent a bond can be prepared according to the following reaction step.

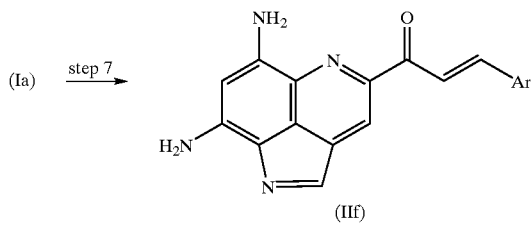

(In the formula, Ar represents substituted or unsubstituted aryl or substituted or unsubstituted heteroaryl which has the same significance as defined above.)

Step 7

Compound (IIf) can be obtained by reaction of Compound (Ia) obtained in process 1 with 1–20 equivalents of an aldehyde represented by ArCHO (wherein Ar has the same significance as defined above) in an inert solvent in the presence of a base.

As the inert solvent, lower alcohols such as methanol and ethanol, ethers such as ether, tetrahydrofuran and dioxane, dimethylformamide, water, etc. may be used alone or as a mixture. As the base, sodium hydroxide, potassium hydroxide, sodium carbonate, potassium carbonate, sodium hydride, potassium tert-butoxide, 1,4-diazabicyclo[2.2.2] octane, 1,8-diazabicyclo[5.4.0]undec-7-ene, etc. may be used in an amount of 0.1–6 equivalents based on Compound (Ia). The reaction is carried out at a temperature between 0° C. and the boiling point of the solvent used, preferably between 0° C. and room temperature for 1–240 hours.

The processes for preparing Compound (III), i.e., Compound (I) wherein $R^1$ represents $CR^{18}R^{19}CH_2CH(OCH_3)_2$ (wherein $R^{18}$ represents hydrogen or is combined with $R^{19}$ to represent =O, and $R^{19}$ represents hydroxy or is combined with $R^{18}$ to represent =O); $R^4$, $R^5$ and $R^6$ represent hydrogen; and $R^2$ and $R^3$ are combined together to represent a bond are described in the following processes 8 and 9.

Process 8

Compound (IIIa), i.e., Compound (III) wherein $R^{18}$ and $R^{19}$ are combined together to represent =O; $R^2$ represents hydrogen; $R^7$ represents hydrogen; and $R^8$ represents acetyl can be prepared according to the following reaction step.

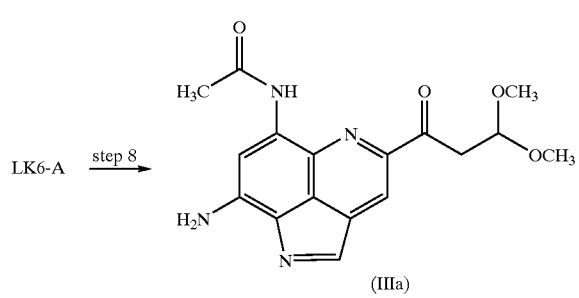

Step 8

Compound (IIIa) can be obtained by reaction of LK6-A with 1–100 equivalents of methanol in an inert solvent, if necessary, in the presence of a base. As the inert solvent, halogen solvents such as dichloromethane and chloroform, ethers such as tetrahydrofuran and dioxane, dimethyl sulfoxide, dimethylformamide, etc. may be used. Methanol may be used also as the solvent. As the base, sodium carbonate, potassium carbonate, sodium hydroxide, potassium hydroxide, 1,4-diazabicyclo[2.2.2]octane, 1,8-diazabicyclo[5.4.0]undec-7-ene, triethylamine, diisopropylethylamine, etc. may be used in an amount of 0.1–20 equivalents based on LK6-A. The reaction is carried out at a temperature between 0° C. and the boiling point of the solvent used, preferably 20–60° C. for 1–48 hours.

Process 9

Compound (IIIb), i.e., Compound (III) wherein $R^{18}$ and $R^{19}$ are combined together to represent =O; $R^2$ represents halogen, $SR^{12}$ (wherein $R^{12}$ has the same significance as defined above) or $NR^{13}R^{14}$ (wherein $R^{13}$ and $R^{14}$ have the same significances as defined above); $R^7$ represents hydrogen; and $R^8$ represents acetyl can be prepared according to the following reaction step.

(IIIa) step 9

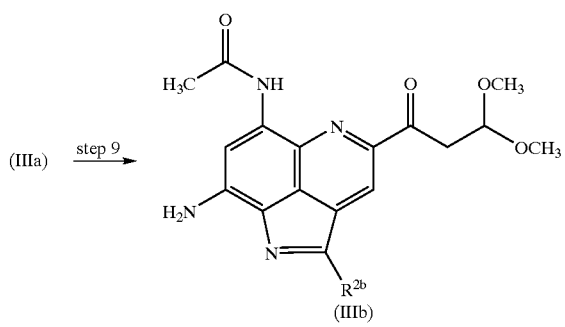

(IIIb)

{In the formula, $R^{2b}$ represents halogen, $SR^{12}$ (wherein $R^{12}$ has the same significance as defined above) or $NR^{13}R^{14}$ (wherein $R^{13}$ and $R^{14}$ have the same significances as defined above).}

The halogen represented by $R^{2b}$ has the same significance as the above halogen.

Step 9

Compound (IIIb) can be obtained by subjecting Compound (IIIa) obtained in step 8 to the reaction similar to that in step 3, step 4 or step 5.

Compound (IIIa) and Compound (IIIb) obtained in step 8 and step 9 can be used as intermediates for further synthesizing novel derivatives. For example, Compound (IIIc), wherein $R^{2b}$ is converted into substituted or unsubstituted lower alkynyl (the lower alkynyl has the same significance as defined above), can be obtained by reaction of Compound (IIIba), i.e., the above Compound (IIIb) wherein $R^{2b}$ is bromine, with substituted or unsubstituted lower alkyne (the lower alkyne includes acetylene, propyne, butyne, pentyne and hexyne having 2–6 carbon atoms) in the presence of an appropriate palladium catalyst according to the method described in the literature [SYNTHESIS, p. 235 (1991)] or a similar method thereto. Further, Compound (IIId), wherein $R^{2b}$ is converted into substituted or unsubstituted aryl or substituted or unsubstituted heteroaryl, can also be obtained by reaction of Compound (IIIba) with various aromatic borate compounds or organic tin compounds instead of lower alkyne, which is known as the Suzuki reaction or the Stille reaction.

Compound (IIIe), wherein $R^{2b}$ is converted into substituted or unsubstituted lower alkyl, can be obtained by subjecting the above Compound (IIIc) to catalytic hydrogenation in an inert solvent in the presence of an appropriate catalyst. As the inert solvent, lower alcohols such as methanol and ethanol, ethyl acetate, dimethylformamide, etc. may be used alone or as a mixture. As the catalyst, any of the catalysts that are usually used in hydrogenation, for example, palladium/carbon and platinum oxide can be used. The reaction is carried out at a temperature between 0° C. and the boiling point of the solvent used, preferably 20–30° C. for 0.5–48 hours.

Compound (IIIf), wherein $R^{2b}$ is converted into substituted or unsubstituted lower alkenyl, can be obtained by using, as a catalyst, lead-treated palladium-calcium carbonate known as the Lindlar catalyst.

Any of these compounds wherein $R^1$ represents $COCH_2CH(OCH_3)_2$ can be converted into a compound wherein the carbonyl group in $R^1$ is reduced, $R^{18}$ represents hydrogen and $R^{19}$ represents hydroxy by reducing the compound wherein $R^1$ represents $COCH_2CH(OCH_3)_2$ with 0.5–10 equivalents of sodium borohydride in an inert solvent. As the inert solvent, lower alcohols such as methanol and ethanol, dichloromethane, chloroform, dimethylformamide, etc. may be used alone or as a mixture. The reaction is carried out at a temperature between −20° C. and the boiling point of the solvent used, preferably 0–30° C. for 0.1–12 hours.

Process 10

Compound (IV), i.e., Compound (I) wherein $R^1$ represents:

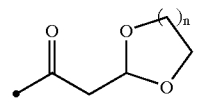

(wherein n has the same significance as defined above); $R^2$, $R^4$, $R^5$ and $R^6$ represent hydrogen; $R^{2'}$ and $R^3$ are combined together to represent a bond; $R^7$ represents hydrogen; and $R^8$ represents acetyl can be prepared according to the following reaction step.

LK6-A step 10

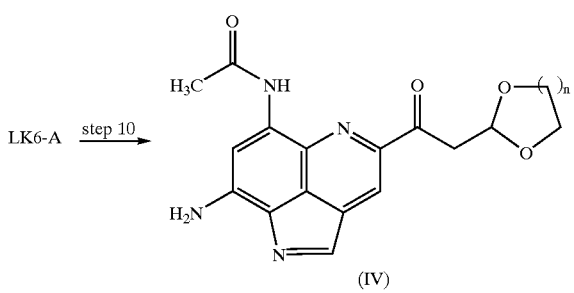

(IV)

(In the formula, n has the same significance as defined above.)

Step 10

Compound (IV) can be obtained by reaction of LK6-A with 1–100 equivalents of ethylene glycol or propylene glycol in an inert solvent, if necessary, in the presence of a base.

As the inert solvent, halogen solvents such as dichloromethane and chloroform, ethers such as tetrahydrofuran and dioxane, dimethyl sulfoxide, dimethylformamide, etc. may be used. Ethylene glycol or propylene glycol may be used also as the solvent.

As the base, sodium carbonate, potassium carbonate, sodium hydroxide, potassium hydroxide, 1,4-diazabicyclo[2.2.2]octane, 1,8-diazabicyclo[5.4.0]undec-7-ene, triethylamine, diisopropylethylamine, etc. may be used in an amount of 0.1–20 equivalents based on LK6-A. The reaction is carried out at a temperature between 0° C. and the boiling point of the solvent used, preferably 20–60° C. for 1–96 hours.

Process 11

Compound (V), i.e., Compound (I) wherein $R^1$ represents (E)-3-methoxyacryloyl; $R^2$ represents hydrogen; $R^{2'}$ and $R^3$ are combined together to represent a bond; $R^4$ represents hydrogen; $R^5$ represents substituted or unsubstituted lower alkoxycarbonyl or substituted or unsubstituted aralkyloxycarbonyl; $R^7$ represents hydrogen; and $R^8$ represents acetyl can be prepared according to the following reaction step.

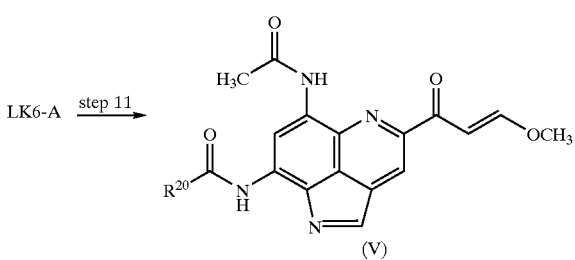

(In the formula, $R^{20}$ represents substituted or unsubstituted lower alkoxy or substituted or unsubstituted aralkyloxy.)

The substituted or unsubstituted lower alkoxy and substituted or unsubstituted aralkyloxy represented by $R^{20}$ have the same significances as the above substituted or unsubstituted lower alkoxy and substituted or unsubstituted aralkyloxy, respectively.

Step 11

Compound (V) can be obtained by reaction of LK6-A with 1–5 equivalents of $ClCOR^{20}$ (wherein $R^{20}$ has the same significance as defined above) in an inert solvent in the presence of a base.

As the inert solvent, dichloromethane, chloroform, methanol, ethanol, dimethylformamide, etc. may be used alone or as a mixture.

As the base, 1,4-diazabicyclo[2.2.2]octane, 1,8-diazabicyclo[5.4.0]undec-7-ene, triethylamine, diisopropylethylamine, etc. may be used in an amount of 1–5 equivalents based on LK6-A. The reaction is carried out at 0–50° C. for 0.1–12 hours.

Process 12

Compound (VI), i.e., Compound (I) wherein $R^1$ represents $COCHR^{15}CH(OCH_3)_2$ (wherein $R^{15}$ represents lower alkyl); $R^2$ represents hydrogen, halogen, $SR^{12}$ (wherein $R^{12}$ has the same significance as defined above) or $NR^{13}R^{14}$ (wherein $R^{13}$ and $R^{14}$ have the same significances as defined above); $R^{2'}$ and $R^3$ are combined together to represent a bond; $R^4$ and $R^5$, which may be the same or different, each represents hydrogen or lower alkyl; $R^7$ represents hydrogen or lower alkyl; and $R^8$ represents acetyl can be prepared according to the following reaction step.

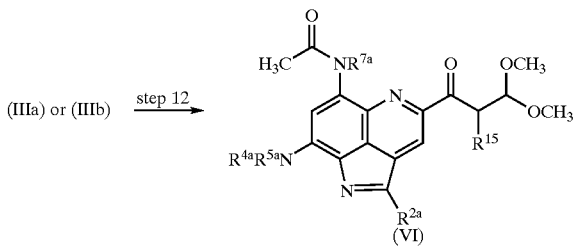

(In the formula, $R^{4a}$ and $R^{5a}$, which may be the same or different, each represents hydrogen or lower alkyl; $R^{7a}$ represents hydrogen or lower alkyl; and $R^{2a}$ and $R^{15}$ have the same significances as defined above.)

The lower alkyl represented by $R^{4a}$, $R^{5a}$ and $R^{7a}$ has the same significance as the above lower alkyl.

Step 12

Compound (VI) can be obtained by reaction of Compound (IIIa) or (IIIb) with 1–10 equivalents of halogenated lower alkyl represented by $R^{15b}X^2$ (wherein $R^{15b}$ represents lower alkyl, and $X^2$ represents halogen, and the lower alkyl represented by $R^{15b}$ and the halogen represented by $X^2$ have the same significances as the above lower alkyl and halogen, respectively) in an inert solvent in the presence of 1–10 equivalents of a base.

Examples of the inert solvent include tetrahydrofuran, dioxane and dimethylformamide, and examples of the base include potassium carbonate, sodium hydride, potassium tert-butoxide and lithium diisopropylamide.

The reaction is carried out at a temperature between −78° C. and the boiling point of the solvent used, preferably 0–30° C. for 0.5–12 hours.

Process 13

Compound (VII), i.e., Compound (I) wherein $R^1$ represents $COCX^3HCH(OCH_3)_2$ (wherein $X^3$ represents halogen, and the halogen represented by $X^3$ has the same significance as the above halogen); $R^2$ represents hydrogen, halogen, $SR^{12}$ (wherein $R^{12}$ has the same significance as defined above) or $NR^{13}R^{14}$ (wherein $R^{13}$ and $R^{14}$ have the same significances as defined above); $R^{2'}$ and $R^3$ are combined together to represent a bond; $R^4$ and $R^5$ represent hydrogen; $R^6$ represents hydrogen or halogen; $R^7$ represents hydrogen; and $R^8$ represents acetyl can be prepared according to the following reaction step.

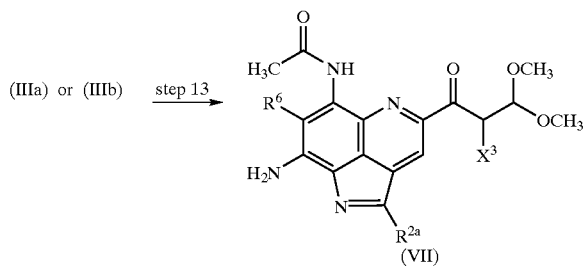

(In the formula, $X^3$, $R^6$ and $R^{2a}$ have the same significances as defined above.)

Step 13

Compound (VII) can be obtained by reaction of Compound (IIIa) or (IIIb) with 1–10 equivalents of a halogenating reagent in an inert solvent, if necessary, in the presence of 1–10 equivalents of a base.

Examples of the base include triethylamine, diisopropylethylamine, potassium carbonate and sodium carbonate. Examples of the halogenating reagent include bromine, chlorine, iodine, N-chlorosuccinimide, N-bromosuccinimide, N-iodosuccinimide, tetrabutylammonium tribromide and pyrrolidone hydrotribromide.

As the inert solvent, dichloromethane, chloroform, carbon tetrachloride, methanol, ethanol, tetrahydrofuran, dioxane, dimethylformamide, etc. may be used alone or as a mixture. The reaction is carried out at a temperature between 0° C. and the boiling point of the solvent used, preferably 20–30° C. for 0.5–24 hours.

Process 14

Compound (VIII), i.e., Compound (I) wherein $R^1$ represents 1-hydroxy-3-methoxypropyl; $R^2$ represents hydrogen, halogen, $SR^{12}$ (wherein $R^{12}$ has the same significance as defined above) or $NR^{13}R^{14}$ (wherein $R^{13}$ and $R^{14}$ have the same significances as defined above); $R^{2'}$ and $R^3$ are combined together to represent a bond; $R^4$ and $R^5$ represent hydrogen; $R^6$ represents hydrogen; $R^7$ represents hydrogen; and $R^8$ represents acetyl can be prepared according to the following reaction step.

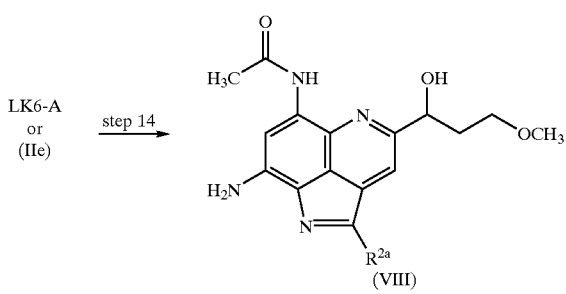

(In the formula, $R^{2a}$ has the same significance as defined above.)

Step 14

Compound (VIII) can be obtained by reducing LK6-A or Compound (IIe) with 1–10 equivalents of sodium borohydride in an inert solvent.

As the inert solvent, lower alcohols such as methanol and ethanol, dichloromethane, chloroform, dimethylformamide, etc. may be used alone or as a mixture.

The reaction is carried out at a temperature between −20° C. and the boiling point of the solvent used, preferably 0–30° C. for 0.1–12 hours.

Process 15

Compound (IX), i.e., Compound (I) wherein $R^1$ represents (E)-3-methoxyacryloyl or $COCH_2CH(OCH_3)_2$; $R^2$ represents hydrogen or substituted or unsubstituted lower alkanoyloxy; $R^{2'}$ represents hydrogen; $R^3$ represents substituted or unsubstituted lower alkanoyl; $R^4$ represents hydrogen; $R^5$ represents substituted or unsubstituted lower alkanoyl; $R^6$ represents hydrogen; $R^7$ represents hydrogen; and $R^8$ represents acetyl can be prepared according to the following reaction step.

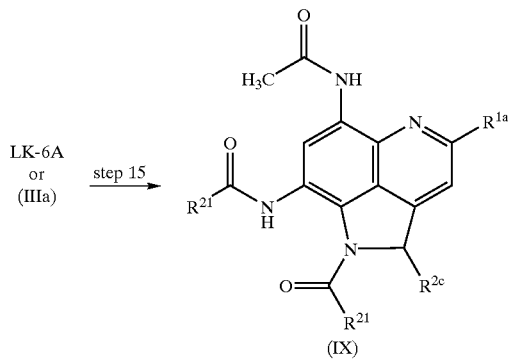

[In the formula, $R^{1a}$ represents (E)-3-methoxyacryloyl or $COCH_2CH(OCH_3)_2$; $R^{2c}$ represents hydrogen or substituted or unsubstituted lower alkanoyloxy; and $R^{21}$ represents substituted or unsubstituted lower alkyl.]

The substituted or unsubstituted lower alkanoyloxy represented by $R^{2c}$ has the same significance as the above substituted or unsubstituted lower alkanoyloxy, and the substituted or unsubstituted lower alkyl represented by $R^{21}$ has the same significance as the above substituted or unsubstituted lower alkyl.

Step 15

Compound (IX) can be obtained by reaction of LK6-A or Compound (IIIa) with 2–100 equivalents of an acid anhydride, if necessary, in an inert solvent.

Examples of the inert solvent include dichloromethane, chloroform and dimethylformaimde, and the acid anhydride may be used also as the solvent. The reaction is carried out at a temperature between 0° C. and the boiling point of the solvent used, preferably 20–30° C. for 1–72 hours.

Further conversion of $R^{2c}$ is possible using Compound (IX) obtained in step 15 as a synthetic intermediate. For example, Compound (IXa), i.e., Compound (IX) wherein $R^{2c}$ is hydrogen can be obtained by hydrogenating the compound wherein $R^{2c}$ is lower alkanoyloxy in an inert solvent in the presence of an appropriate catalyst. As the inert solvent, lower alcohols such as methanol and ethanol, ethyl acetate, dimethylformamide, etc. may be used alone or as a mixture. Appropriate catalysts include those conventionally used in hydrogenation, for example, palladium/carbon and platinum oxide.

The reaction is carried out at a temperature between 0° C. and the boiling point of the solvent used, preferably 20–30° C. for 0.5–48 hours.

The above Compounds (I)–(IX) can be obtained by appropriately combining the above-described methods. Further, Compounds (I) described in the present invention can be obtained by combining methods conventionally used in synthetic organic chemistry.

The desired compounds in the processes described above can be purified by appropriate combinations of purification methods conventionally used in synthetic organic chemistry, for example, filtration, extraction, washing, drying, concentration, crystallization and various kinds of chromatography. The intermediates may be subjected to the subsequent reaction without purification.

In the case where a salt of Compound (I) is desired and it is produced in the form of the desired salt, it can be subjected to purification as such. In the case where Compound (I) is produced in the free state and its salt is desired, the salt can be formed according to a conventional method, that is, by dissolving or suspending Compound (I) in a suitable solvent and adding a desired acid or base thereto.

Compounds (I) and pharmaceutically acceptable salts thereof may exist in the form of adducts with water or various solvents, which are also within the scope of the present invention.

Compounds (I) and pharmaceutically acceptable salts thereof can be used as such or in various pharmaceutical forms according to the pharmacological activity and the purpose of administration. Pharmaceutical compositions of the present invention can be prepared by uniformly mixing an effective amount of Compound (I) or a pharmaceutically acceptable salt thereof, as an active ingredient, with a pharmaceutically acceptable carrier. The carrier can take a wide variety of forms according to the pharmaceutical form desirable for administration. These pharmaceutical compositions are preferably in a unit dose form suitable for oral administration or parenteral administration in the form of ointment, injection, or the like.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 1–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 1–300 mg of the active ingredient.

Syrup can be prepared using sugars such as sucrose, water, ethanol, and the like in a conventional manner.

Ointment-can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injections can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic acid ester and chlorobutanol, antioxidants such as ascorbic acid and sodium pyrosulfite, and the like in a conventional manner.

Compounds (I) and pharmaceutically acceptable salts thereof can be administered orally or parenterally as an ointment, injection, or the like. The effective dose and the administration schedule of Compound (I) or a pharmaceutically acceptable salt thereof will vary depending on the mode of administration, the patient's age, body weight and condition, etc. However, it is generally preferred to administer Compound (I) or a pharmaceutically acceptable salt thereof in a dose of 0.01–20 mg/kg 1–4 times a day.

Examples of Compounds (I) obtained by the present invention are shown in Tables 1 and 2.

TABLE 1

| Compound No. | Example No. | $R^1$ | $R^2$ |
|---|---|---|---|
| 1 | 1 | —C(O)CH=CH—NH$_2$ | H |
| 2 | 2 | —C(O)CH=CH—N(CH$_3$)$_2$ | H |
| 3 | 3 | —C(O)CH=CH—N(CH$_3$)$_2$ | N(CH$_3$)$_2$ |
| 4 | 4 | —C(O)CH=CH—N(CH$_2$CH$_3$)$_2$ | H |
| 5 | 5 | —C(O)CH=CH—N(piperidinyl) | H |
| 6 | 5 | —C(O)CH=CH—N(piperidinyl) | piperidinyl |

TABLE 1-continued

| Compound No. | Example No. | R¹ | (other) |
|---|---|---|---|
| 7 | 6 | CH₃-C(=O)-CH=CH-N(piperazine-N'-CH₃) | H |
| 8 | 7 | CH₃-C(=O)-CH=CH-N(morpholine) | H |
| 9 | 8 | CH₃-C(=O)-CH=CH-N(CH₂Ph)₂ | H |
| 10 | 9 | CH₃-C(=O)-CH=CH-N(CH₂CH₂OH)₂ | H |

Core structure:

8-NHCOCH₃, 5-R¹, with H₂N at position on fused pyrrolo[pyridine] ring system (aminoacetamido-substituted tricyclic heteroaromatic bearing NHCOCH₃ and H₂N groups and R¹ on pyridine nitrogen-containing ring).

| Compound No. | Example No. | R¹ |
|---|---|---|
| 11 | 10 | CH₃-C(=O)-CH=CH-NH-CH₂CH₂OH |
| 12 | 11 | CH₃-C(=O)-CH=CH-NH-(2-amino-2-deoxy hexopyranose; OH, OH, OH, CH₂OH, anomeric OH) |
| 13 | 12 | CH₃-C(=O)-CH=CH-NH-(2-amino-2-deoxy hexopyranose; OH, OH, OH, CH₂OH, anomeric OH) |

TABLE 1-continued
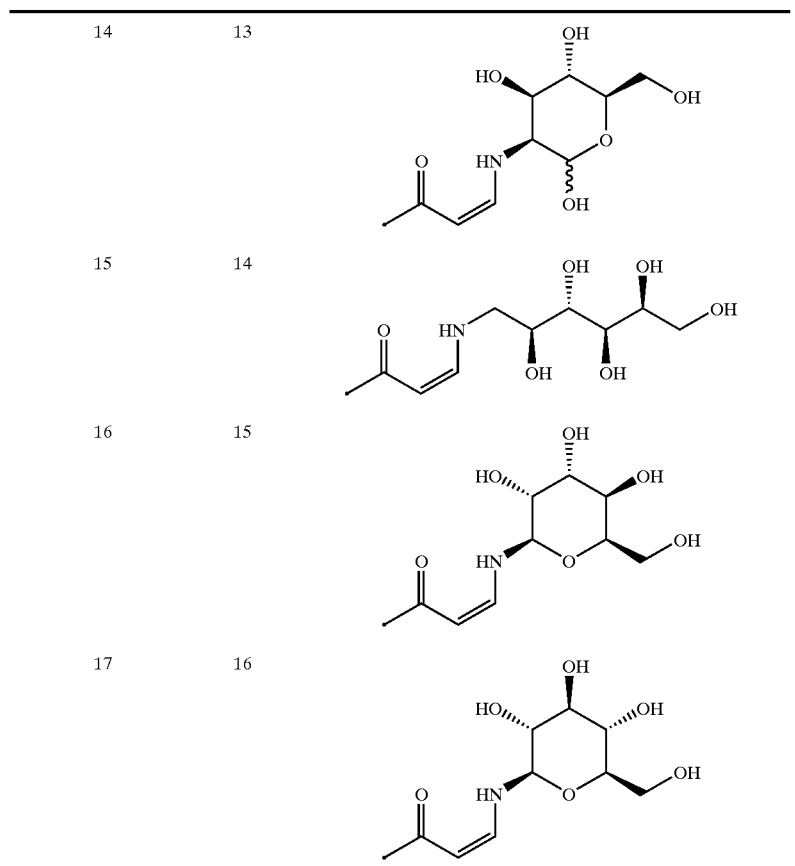
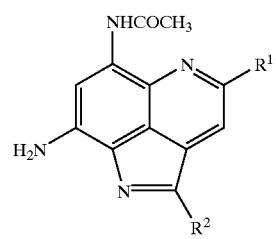
| Compound No. | Example No. | R¹ | R² |
|---|---|---|---|
| 18 | 17 | (ketone)-CH=CH-OCH₃ | 2-(acetamido)-3,4,6-tri-O-acetyl-thio-pyranose |
| 19 | 18 | (ketone)-CH=CH-OCH₃ | 2,3,4,6-tetra-O-acetyl-thio-pyranose |
| 20 | 19 | (ketone)-CH=CH-OCH₃ | SCH₂CH₃ |

TABLE 1-continued
| | | | |
|---|---|---|---|
| 21 | 20 | 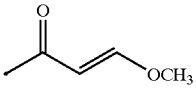 | 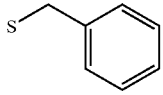 |
| 22 | 21 | 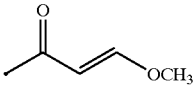 | Cl |
| 23 | 22 | 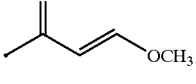 | Br |
| 24 | 23 | 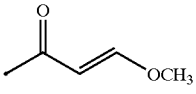 | I |
| 25 | 24 | 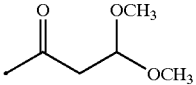 | H |
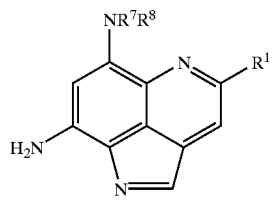
| Compound No. | Example No. | R$^1$ | R$^7$ | R$^8$ |
|---|---|---|---|---|
| 26 | 25 | 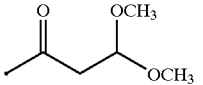 | H | H |
| 27 | 26 | 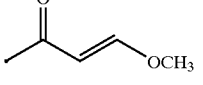 | H | H |
| 28 | 27 | 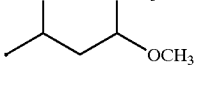 | H | COCH$_3$ |
| 29 | 28 | 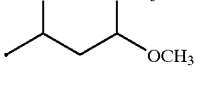 | H | H |
| 30 | 29 | 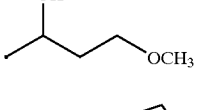 | H | COCH$_3$ |
| 31 | 30 | 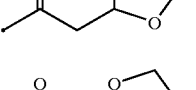 | H | COCH$_3$ |
| 32 | 30 | 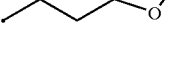 | H | H |

TABLE 1-continued
| | | | | |
|---|---|---|---|---|
| 33 | 31 | 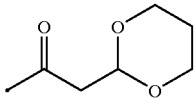 | H | COCH$_3$ |
| 34 | 31 | 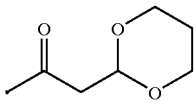 | H | H |
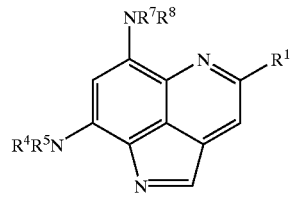
| Compound No. | Example No. | R$^1$ | R$^5$ | R$^4$ | R$^8$ | R$^7$ |
|---|---|---|---|---|---|---|
| 35 | 32 | 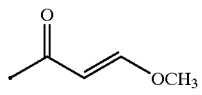 | CO$_2$CH$_3$ | H | COCH$_3$ | H |
| 36 | 33 | 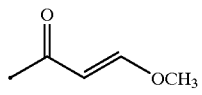 | CO$_2$CH$_2$CH$_3$ | H | COCH$_3$ | H |
| 37 | 34 | 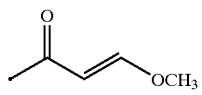 | CO$_2$(CH$_2$)$_2$CH$_3$ | H | COCH$_3$ | H |
| 38 | 35 | 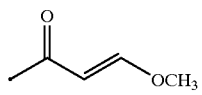 | CO$_2$(CH$_2$)$_3$CH$_3$ | H | COCH$_3$ | H |
| 39 | 36 | 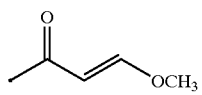 | CO$_2$(CH$_2$)$_7$CH$_3$ | H | COCH$_3$ | H |
| 40 | 37 | 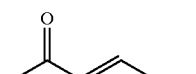 | CO$_2$CH$_2$Ph | H | COCH$_3$ | H |
| 41 | 38 | 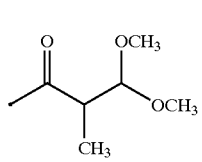 | CH$_3$ | CH$_3$ | COCH$_3$ | CH$_3$ |
| 42 | 39 | 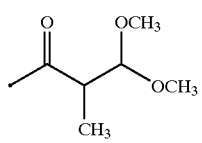 | CH$_3$ | CH$_3$ | CH$_3$ | CH$_3$ |
| 43 | 39 | 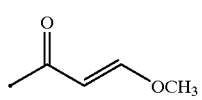 | CH$_3$ | CH$_3$ | CH$_3$ | CH$_3$ |

TABLE 1-continued
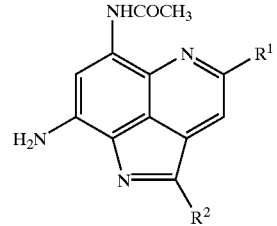
| Compound No. | Example No. | R¹ | R² |
|---|---|---|---|
| 44 | 40 | 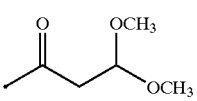 | Br |
| 45 | 41 | 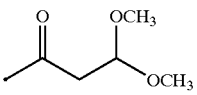 | N(CH₃)₂ |
| 46 | 42 | 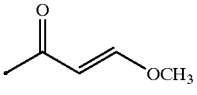 | N(CH₃)₂ |
| 47 | 43 | 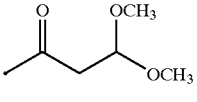 |  |
| 48 | 44 | 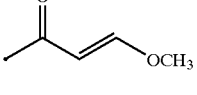 |  |
| 49 | 45 | 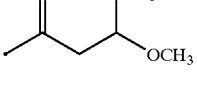 | 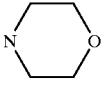 |
| 50 | 46 | 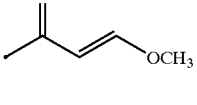 | 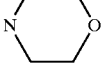 |
| 51 | 47 | 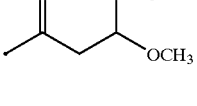 | N₃ |
| 52 | 48 | 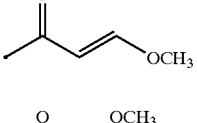 | N₃ |
| 53 | 49 | 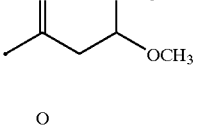 | 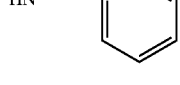 |
| 54 | 50 | 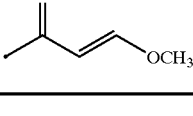 | 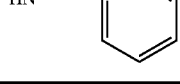 |

TABLE 1-continued
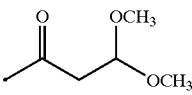
| Compound No. | Example No. | R¹ | R² |
|---|---|---|---|
| 55 | 51 | 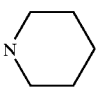 | 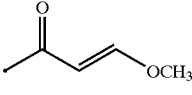 |
| 56 | 52 | 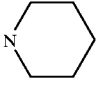 | 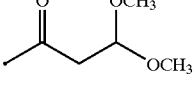 |
| 57 | 53 | 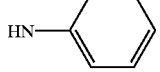 | 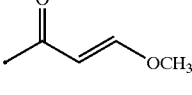 |
| 58 | 54 | 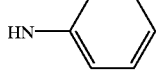 | 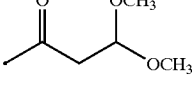 |
| 59 | 55 | 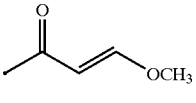 | NH(CH$_2$)$_3$CH$_3$ |
| 60 | 56 | 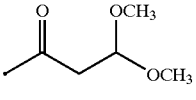 | NH(CH$_2$)$_3$CH$_3$ |
| 61 | 57 | 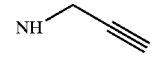 | 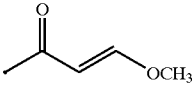 |
| 62 | 58 | 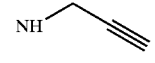 | 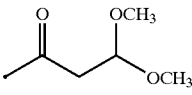 |
| 63 | 59 | 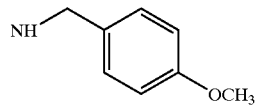 | 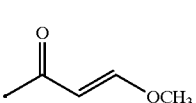 |
| 64 | 60 | 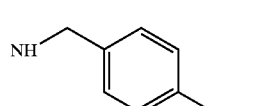 | |

TABLE 1-continued

| Compound No. | Example No. | R¹ | R² |
|---|---|---|---|
| 65 | 61 | CH₃-CO-CH₂-CH(OCH₃)₂ | N(CH₂CH₃)₂ |
| 66 | 62 | CH₃-CO-CH=CH-OCH₃ | N(CH₂CH₃)₂ |
| 67 | 63 | CH₃-CO-CH₂-CH(OCH₃)₂ | pyrrolidin-1-yl |
| 68 | 64 | CH₃-CO-CH=CH-OCH₃ | pyrrolidin-1-yl |
| 69 | 65 | CH₃-CO-CH₂-CH(OCH₃)₂ | 4-hydroxypiperidin-1-yl |
| 70 | 66 | CH₃-CO-CH=CH-OCH₃ | 4-hydroxypiperidin-1-yl |
| 71 | 67 | CH₃-CO-CH₂-CH(OCH₃)₂ | NHCH₂CH₂OCH₃ |
| 72 | 68 | CH₃-CO-CH=CH-OCH₃ | NHCH₂CH₂OCH₃ |
| 73 | 69 | CH₃-CO-CH₂-CH(OCH₃)₂ | C≡CH |
| 74 | 70 | CH₃-CO-CH=CH-OCH₃ | C≡CH |

TABLE 1-continued
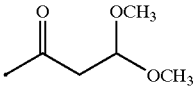
| Compound No. | Example No. | R¹ | R² | R⁶ | R⁷ | R⁸ |
|---|---|---|---|---|---|---|
| 75 | 71 | 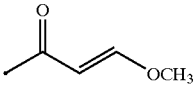 | $CH_2CH_3$ | H | H | $COCH_3$ |
| 76 | 72 | 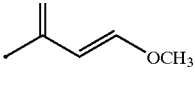 | $COCH_3$ | H | H | $COCH_3$ |
| 77 | 73 | 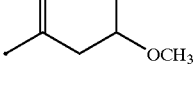 | $CH_2CH_3$ | H | H | $COCH_3$ |
| 78 | 74 | 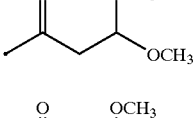 | Br | H | H | H |
| 79 | 74 | 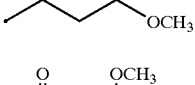 | Br | Br | H | H |
| 80 | 75 | 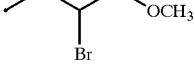 | H | Br | H | H |
| 81 | 76 | 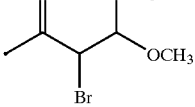 | Br | H | H | $COCH_3$ |
| 82 | 77 | 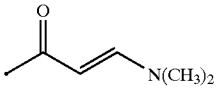 | Br | Br | H | $COCH_3$ |
| 83 | 78 | 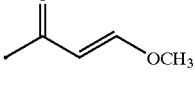 | Br | H | H | $COCH_3$ |
| 84 | 79 | 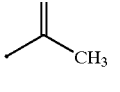 | Br | H | H | H |
| 85 | 80 |  | H | H | H | H |

TABLE 1-continued
| Compound No. | Example No. | | | | | |
|---|---|---|---|---|---|---|
| 86 | 81 | 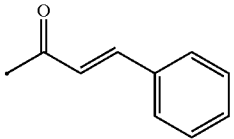 | H | H | H | H |
| 87 | 82 | 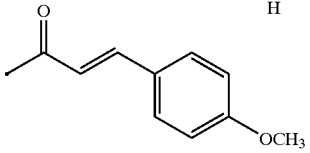 | H | H | H | H |
| 88 | 83 | 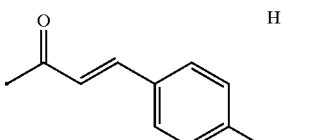 | H | H | H | H |
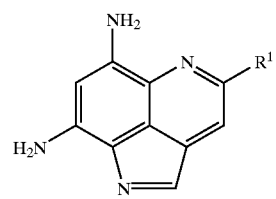
| Compound No. | Example No. | R¹ |
|---|---|---|
| 89 | 84 | 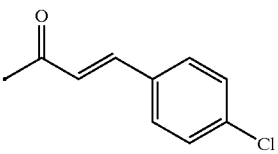 |
| 90 | 85 | 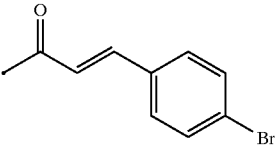 |
| 91 | 86 | 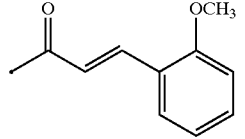 |
| 92 | 87 | 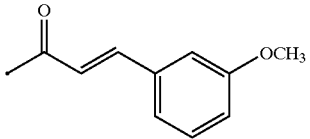 |
| 93 | 88 | 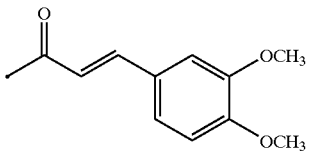 |

TABLE 1-continued
| 94 | 89 | 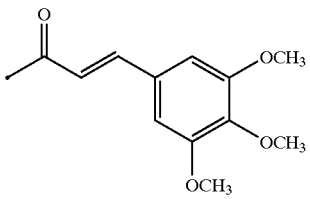 |
| 95 | 90 | 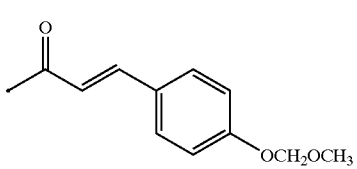 |
| 96 | 91 | 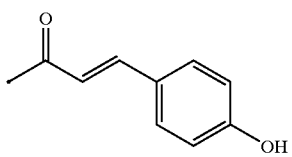 |
| 97 | 92 | 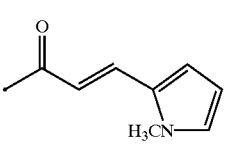 |
| 98 | 93 | 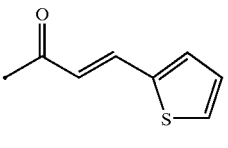 |
| 99 | 94 | 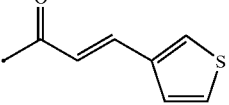 |
| 100 | 95 | 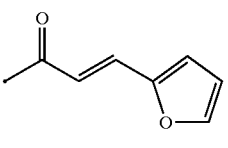 |
| 101 | 96 | 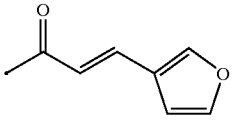 |
| 102 | 97 | 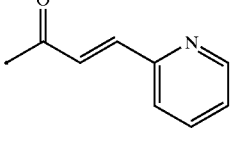 |
| 103 | 98 | 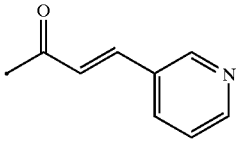 |

TABLE 1-continued
| 104 | 99 | 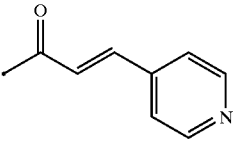 |
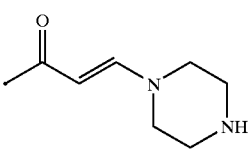
| Compound No. | Example No. | R¹ |
| --- | --- | --- |
| 105 | 100 | 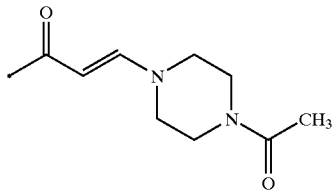 |
| 106 | 101 | 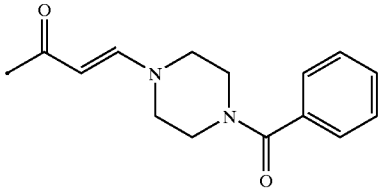 |
| 107 | 102 | 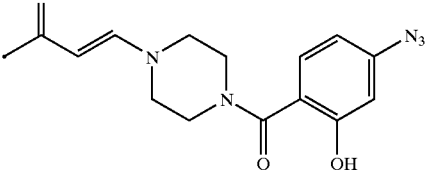 |
| 108 | 103 | 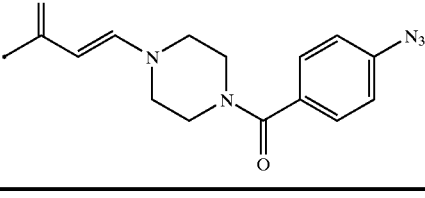 |
| 109 | 104 | |
Ph: 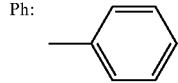
Ac: COCH₃

TABLE 2

[Structure: core scaffold with NHCOCH₃ group, N-acetyl group, pyrrolo-quinoline system with R¹ and R² substituents]

| Compound No. | Example No. | R¹ | R² |
|---|---|---|---|
| 110 | 105 | −C(O)−CH=CH−OCH₃ | OCOCH₃ |
| 111 | 106 | −C(O)−CH(OCH₃)−CH₂−OCH₃ | OCOCH₃ |
| 112 | 107 | −C(O)−CH(OCH₃)−CH₂−OCH₃ | H |
| 113 | 107 | −C(O)−CH(OH)−CH₂−OCH₃ | H |
| 114 | 108 | −C(O)−CH₂−CH₂−OCH₃ | H |

The immunosuppressive activity of typical Compounds (I) is described below.

TEST EXAMPLE 1

Growth Inhibition Against T Cells in Mixed Mouse Lymphocyte Reaction

Lymph node was aseptically excised from a B10.BR mouse (Japan SLC Inc.) and washed with a solution comprising Hanks' balanced salt solution (HBSS, Gibco) and 2.5% fetal calf serum (FCS, Gibco) (HBSS-FCS). To the washed lymph node was added RPMI1640 medium comprising 10% FCS, 1% 200 mM L-glutamine, a 1% penicillin-streptomycin solution, 5% NCTC-109, 1% 1 M HEPES (all produced by Gibco), 7.5% sodium hydrogen carbonate and 0.1% 50 mM 2-mercaptoethanol (hereinafter referred to as RPMI1640-FCS) to prepare a single cell suspension having a density of $3\times10^6$ cells/ml.

Separately, spleen was aseptically excised from an AKR mouse (Japan SLC Inc.) to prepare a single cell suspension with HBSS-FCS. To the obtained cell suspension was added mitomycin C (MMC) (Kyowa Hakko Kogyo Co., Ltd.) to a final concentration of 0.05 mg/ml, followed by incubation at 37° C. for 30 minutes. Then, the suspension was washed three times with HBSS-FCS, and a single cell suspension having a density of $1\times10^7$ cells/ml was prepared using RP1640-FCS.

Into each well of a 96-well microtiter plate were put 0.05 ml of the B10. BR mouse lymph node cell suspension (containing $1.5\times10^5$ cells), 0.05 ml of the AKR mouse spleen cell suspension (containing $5\times10^5$ cells) and 0.1 ml of a solution of Compound (I) in RPMI1640-FCS at each test concentration, followed by incubation in a $CO_2$ incubator at 37° C. for 72 hours. The solutions of the test compound were prepared to give final concentrations of $7\times10^{-10}$–$7\times10^{-6}$ M.

[³H]-Thymidine was added to the wells in an amount of $1\times10^{-6}$ Ci, 18 hours before the end of incubation. After the incubation, the cells were collected on filter paper with a cell harvester, followed by drying. A toluene scintillator was added to the cells, and the radioactivity of [³H]-thymidine incorporated into the cells was determined using a liquid scintillation counter (test group).

As a control group, 0.1 ml of RPMI1640-FCS containing no test compound was added, followed by incubation in the same manner as above, and the radioactivity of [³H]-thymidine incorporated into the cells was determined. To 0.05 ml of the B10.BR mouse lymph node cell suspension (containing $1.5\times10^5$ cells) or 0.05 ml of the AKR mouse spleen cell suspension (containing $5\times10^5$ cells) was added 0.15 ml of RPMI1640-FCS, followed by incubation in the same manner as above, and the radioactivity of [³H]-thymidine incorporated into the cells was determined.

The T cell growth inhibition rate was calculated according to the following equation.

$$T \text{ cell growth inhibition rate } (\%) = (C-T)/\{C-(A+B)\}\times 100$$

C: Radioactivity of the control group
T: Radioactivity of the test group
A: Radioactivity of the MMC-treated AKR mouse
B: Radioactivity of the B10.BR mouse (In the equation, the radioactivity of the MMC-treated AKR mouse refers to the radioactivity of [³H]-thymidine incorporated, into the MMC-treated AKR mouse spleen cells, and the radioactivity of the B10.BR mouse refers to the radioactivity of [³H]-thymidine incorporated into the B10.BR mouse lymph node cells.)

The 50% inhibitory concentration of each compound against the growth of T cells in mixed mouse lymphocyte reaction was calculated from the above equation. The results are shown in Table 3.

TABLE 3

| Compound No. | 50% Inhibitory concentration ($\mu$M) |
|---|---|
| 1 | 0.018 |
| 2 | 0.25 |
| 4 | 0.25 |
| 5 | 0.098 |
| 7 | 0.048 |
| 8 | 0.058 |
| 9 | 0.38 |
| 10 | 0.15 |
| 11 | 0.072 |
| 12 | 0.050 |
| 13 | 0.058 |
| 14 | 0.044 |
| 15 | 0.038 |
| 20 | 0.68 |
| 22 | 0.15 |
| 23 | 0.65 |
| 24 | 0.45 |
| 25 | 0.032 |
| 27 | 0.11 |
| 31 | 0.0090 |
| 32 | 0.41 |
| 33 | 0.42 |

TABLE 3-continued

| Compound No. | 50% Inhibitory concentration ($\mu$M) |
| --- | --- |
| 50 | 0.46 |
| 52 | 0.091 |
| 73 | 0.54 |
| 74 | 0.16 |
| 76 | 0.20 |
| 88 | 0.88 |
| 94 | 0.88 |

TEST EXAMPLE 2

Effect on Delayed Type Hypersensitivity of Sole

Balb/c strain male mice (8-weeks-old, Charles River) were immunized by subcutaneous administration of 0.1 ml of 2,4,6-trinitrobenzene sulfonic acid (TNBS) (adjusted to 10 mM with a phosphate buffer) into the right side. The test was carried out using groups of mice, each group consisting of 5 animals, which are a control group treated with 0.3% methyl cellulose containing 3% DMSO, a group treated with a fixed concentration of a test compound suspended in 0.3% methyl cellulose containing 3% DMSO, and a group treated with cyclosporin A (Sandoz Pharmaceuticals, Ltd.).

The 0.3% methyl cellulose containing 3% DMSO or the test compound was intraperitoneally administered to the mice 30 minutes before the immunization treatment and thereafter every 24 hours, totally 5 times. Cyclosporin A was orally administered one hour before the immunization treatment and thereafter every 24 hours, totally 5 times. On the fifth day when sensitization was established, 0.05 ml of the above 10 mM TNBS as a causative antigen was subcutaneously injected into the right hind sole. Eighteen hours after the injection, the thickness of both feet of each mouse of the groups treated with respective amounts of test compound was measured with Dial Thickness Gauge. The value (T) was obtained by subtracting the thickness of the left foot from that of the right foot. Separately the thickness of both feet of each mouse of the group treated with no test compound was measured and the value (C) was obtained by subtracting the thickness of the left foot from that of the right foot. The suppression rate (%) was determined according to the equation [(C−T)/C]×100 (%). The results are shown in Table 4.

TABLE 4

| Compound No. | Dose (mg/kg) | Suppression rate (%) |
| --- | --- | --- |
| 25 | 30 | 77 |
| Cyclosporin A | 30 | 83 |

As can be seen from Tables 3 and 4, Compounds (I) have an excellent immunosuppressive activity and are useful as therapeutic agents for autoimmune diseases, allergic diseases, infections caused by organ transplantation, etc. Compounds (I) are also useful as therapeutic agents for diseases caused by abnormal cell growth such as leukemia and cancers.

BEST MODES FOR CARRYING OUT THE INVENTION

Certain embodiments of the present invention are illustrated in the following examples.

The physicochemical properties of the compounds shown in examples below were determined using the following instruments.

$^1$H NMR:
  JEOL Alpha 400 (400 MHz)
  JEOL Lambda 300 (300 MHz)
  Bruker DMX-500 (500 MHz)
FABMS:
  JEOL JMS-HX110

The peak ($\delta$) in the proton nuclear magnetic resonance spectrum ($^1$H NMR) used in examples is expressed in unit of 1/1000000 (ppm) toward lower magnetic field from tetramethylsilane. The observed form, the coupling constant and the number of proton are shown, in the order given, in the parenthesis after the value of $\delta$ of each signal. In the $^1$H NMR data, br means that the signal is broad.

EXAMPLE 1

Compound 1

LK6-A (48.0 mg, 0.15 mmol) was dissolved in dimethyl sulfoxide (8 ml), and 28% aqueous ammonia (0.15 ml) was added thereto, followed by stirring at room temperature for 14 hours. After the reaction mixture was diluted with chloroform, the resulting diluted solution was passed through a silica gel column for adsorption, followed by elution with chloroform/methanol (93:7), whereby Compound 1 (38.0 mg, 83%) was obtained.

$^1$H NMR (400 MHz, DMSO-$d_6$) $\delta$ 2.34 (s, 3H), 6.81 (d, J=7.3 Hz, 1H), 7.25 (ddd, J=14.6, 7.3, 7.3 Hz, 1H), 7.77 (br dd, J=7.3, 5.7 Hz, 1H), 8.02 (br s, 2H), 8.10 (s, 1H), 8.34 (s, 1H), 8.59 (s, 1H), 9.46 (br dd, J=14.6, 5.7 Hz, 1H), 9.94 (br s, 1H)

FABMS m/z 296 (M+H)$^+$ $C_{15}H_{13}N_5O_2$=295.

EXAMPLE 2

Compound 2

LK6-A (39.1 mg, 0.13 mmol) was dissolved in dimethyl sulfoxide (8 ml), and 50% aqueous dimethylamine (0.16 ml) was added thereto, followed by stirring at room temperature for 3.5 hours. To the reaction mixture was added water, and the resulting mixture was extracted with chloroform. The organic layer was washed twice with water and then dried over anhydrous sodium sulfate. After the solvent was evaporated under reduced pressure, the residue was purified by silica gel column chromatography with chloroform/methanol (9:1), whereby Compound 2 (24.8 mg, 61%) was obtained.

$^1$H NMR (500 MHz, DMSO-$d_6$) $\delta$ 2.34 (s, 3H), 3.06 (br s, 3H), 3.19 (br s, 3H), 6.93 (br d, J=12.7 Hz, 1H), 7.83 (d, J=12.7 Hz, 1H), 8.01 (br s, 2H), 8.11 (s, 1H), 8.34 (s, 1H), 8.60 (s, 1H), 10.1 (br s, 1H)

FABMS m/z 324 (M+H)$^+$ $C_{17}H_{17}N_5O_2$=323.

EXAMPLE 3

Compound 3

LK6-A (20.5 mg, 0.07 mmol) was dissolved in dimethyl sulfoxide (6 ml), and 50% aqueous dimethylamine (2 ml) was added thereto, followed by stirring at room temperature for 2.5 hours. To the reaction mixture was added water, and the resulting mixture was extracted three times with chloroform. The organic layers were combined and dried over anhydrous sodium sulfate. After the solvent was evaporated under reduced pressure, the residue was purified by silica gel column chromatography with chloroform/methanol (9:1), whereby Compound 3 (16.0 mg, 66%) was obtained.

$^1$H NMR (500 MHz, CDCl$_3$) δ 2.37 (s, 3H), 3.06 (br s, 3H), 3.22 (br s, 3H), 3.47 (s, 6H), 4.85 (br s, 2H), 6.63 (d, J=12.6 Hz, 1H), 7.96 (d, J=12.6 Hz, 1H), 8.15 (s, 1H), 8.70 (s, 1H), 9.04 (br s, 1H)

FABMS m/z 367 (M+H)$^+$ C$_{19}$H$_{22}$N$_6$O$_2$=366.

EXAMPLE 4

Compound 4

LK6-A (100 mg, 0.31 mmol) was dissolved in dimethyl sulfoxide (10 ml), and diethylamine (0.096 ml, 0.93 mmol) was added thereto, followed by stirring at room temperature for 50 minutes. To the reaction mixture was added water, and the resulting mixture was extracted with chloroform. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (14:1) and preparative thin layer chromatography with chloroform/methanol (9:1), followed by trituration with isopropyl ether, whereby Compound 4 (47.0 mg, 43%) was obtained.

$^1$H NMR (500 MHz, DMSO-d$_6$) δ 1.1–1.2 (m, 6H), 2.28 (s, 3H), 3.3–3.5 (m, 4H), 6.90 (br d, J=12.7 Hz, 1H), 7.77 (d, J=12.9 Hz, 1H), 7.97 (br s, 2H), 8.02 (s, 1H), 8.30 (s, 1H), 8.54 (s, 1H), 9.97 (s, 1H)

FABMS m/z 352 (M+H)$^+$ C$_{19}$H$_{21}$N$_5$O$_2$=351.

EXAMPLE 5

Compounds 5 and 6

LK6-A (29.8 mg, 0.10 mmol) was dissolved in dimethyl sulfoxide (6 ml), and piperidine (0.050 ml) was added thereto, followed by stirring at room temperature for 15 hours. To the reaction mixture was added water, and the resulting mixture was extracted with chloroform. The organic layer was washed twice with water and then dried over anhydrous sodium sulfate. After the solvent was evaporated under reduced pressure, the residue was purified by silica gel column chromatography with chloroform/methanol/triethylamine (97:1:2), whereby Compound 5 (16.2 mg, 46%) and Compound 6 (11.0 mg, 26%) were obtained.

Compound 5: $^1$H NMR (400 MHz, DMSO-d$_6$) δ 1.64 (m, 6H), 2.36 (s, 3H), 3.54 (m, 4H), 7.05 (d, J=12.9 Hz, 1H), 7.82 (d, J=12.9 Hz, 1H), 8.16 (s, 1H), 8.31 (br s, 2H), 8.43 (s, 1H), 8.67 (s, 1H), 10.2 (s, 1H)

FABMS m/z 364 (M+H)$^+$ C$_{20}$H$_{21}$N$_5$O$_2$=363.

Compound 6: $^1$H NMR (400 MHz, CD$_3$OD) δ 1.76 (m, 6H), 1.81 (m, 6H), 2.33 (s, 3H), 3.6 (m, 4H), 3.9 (m, 4H), 6.79 (d, J=12.7 Hz, 1H), 8.01 (d, J=12.7 Hz, 1H), 8.08 (s, 1H), 8.61 (s, 1H)

FABMS m/z 447 (M+H)$^+$ C$_{25}$H$_{30}$N$_6$O$_2$=446.

EXAMPLE 6

Compound 7

LK6-A (31.0 mg, 0.10 mmol) was dissolved in dimethyl sulfoxide (6 ml), and N-methylpiperazine (0.050 ml) was added thereto, followed by stirring at room temperature for 3.5 hours. To the reaction mixture was added water, and the resulting mixture was extracted with chloroform. The organic layer was washed twice-with water and then dried over anhydrous sodium sulfate. After the solvent was evaporated under reduced pressure, the residue was purified by silica gel column chromatography with chloroform/methanol (4:1), whereby Compound 7 (28.0 mg, 74%) was obtained.

$^1$H NMR (400 MHz, DMSO-d$_6$) δ 2.24 (s, 3H), 2.35 (s, 3H), 2.43 (m, 4H), 3.56 (m, 4H), 7.09 (d, J=12.8 Hz, 1H), 7.80 (d, J=12.8 Hz, 1H), 8.01 (br s, 2H), 8.13 (s, 1H), 8.34 (s, 1H), 8.61 (s, 1H), 10.1 (s, 1H)

FABMS m/z 379 (M+H)$^+$ C$_{20}$H$_{22}$N$_6$O$_2$=378.

EXAMPLE 7

Compound 8

LK6-A (29.9 mg, 0.10 mmol) was dissolved in dimethyl sulfoxide (6 ml), and morpholine (0.050 ml) was added thereto, followed by stirring at room temperature for 5 hours. To the reaction mixture was added water, and the resulting mixture was extracted with chloroform. The organic layer was washed twice with water and then dried over anhydrous sodium sulfate. After the solvent was evaporated under reduced pressure, the residue was purified by silica gel column chromatography with chloroform/methanol/triethylamine (97:1:2), whereby Compound 8 (24.8 mg, 70%) was obtained.

$^1$H NMR (400 MHz, DMSO-d$_6$) δ 2.37 (s, 3H), 3.60 (m, 4H), 3.71 (m, 4H), 7.12 (d, J=12.8 Hz, 1H), 7.87 (d, J=12.8 Hz, 1H), 8.23 (s, 1H), 8.61 (s, 1H), 8.78 (s, 1H), 8.92 (br s, 2H), 10.3 (s, 1H)

FABMS m/z 366 (M+H)$^+$ C$_{19}$H$_{19}$N$_5$O$_3$=365.

EXAMPLE 8

Compound 9

LK6-A (49.1 mg, 0.16 mmol) was dissolved in dimethyl sulfoxide (10 ml), and dibenzylamine (0.10 ml) was added thereto, followed by stirring at room temperature for 48 hours. To the reaction mixture was added water, and the resulting mixture was extracted with chloroform. The organic layer was washed twice with water and then dried over anhydrous sodium sulfate. After the solvent was evaporated under reduced pressure, the residue was purified by silica gel column chromatography with chloroform/methanol (39:1), whereby Compound 9 (55.4 mg, 74%) was obtained.

$^1$H NMR (400 MHz, DMSO-d$_6$) δ 2.27 (s, 3H), 4.67 (s, 2H), 4.70 (s, 2H), 7.18 (d, J=12.9 Hz, 1H), 7.2–7.4 (m, 1H), 8.04 (br s, 2H), 8.06 (s, 1H), 8.12 (d, J=12.9 Hz, 1H), 8.33 (s, 1H), 8.59 (s, 1H), 9.92 (s, 1H)

FABMS m/z 476 (M+H)$^+$ C$_{29}$H$_{25}$N$_5$O$_2$=475.

EXAMPLE 9

Compound 10

LK6-A (28.8 mg, 0.09 mmol) was dissolved in dimethyl sulfoxide (6 ml), and diethanolamine (0.050 ml) was added thereto, followed by stirring at room temperature for 15 hours. The reaction mixture was diluted with chloroform, and the resulting diluted solution was passed through a silica gel column for adsorption, followed by elution with chloroform/methanol (4:1), whereby Compound 10 (25.6 mg, 72%) was obtained.

$^1$H NMR (400 MHz, DMSO-d$_6$) δ 2.32 (s, 3H), 3.5–3.8 (m, 8H), 4.8–4.9 (m, 2H), 6.93 (br d, J=13 Hz, 1H), 7.81 (d,

J=12.9 Hz, 1H), 8.01 (br s, 2H), 8.06 (s, 1H), 8.34 (s, 1H), 8.57 (s, 1H), 9.93 (s, 1H)
FABMS m/z 384 (M+H)$^+$ C$_{19}$H$_{21}$N$_5$O$_4$=383.

EXAMPLE 10

Compound 11

LK6-A (60 mg, 0.19 mmol) was dissolved in dimethyl sulfoxide (4 ml), and ethanolamine (0.030 ml, 0.50 mmol) was added thereto, followed by stirring at room temperature for 24 hours. Then, the reaction mixture was poured into water (200 ml) and the resulting mixture was allowed to stand at 5° C. for 3 days for precipitation. The precipitate was separated by filtration through a membrane filter, whereby Compound 11 (35.4 mg, 54%) was obtained.

$^1$H NMR (400 MHz, DMSO-d$_6$) δ 2.34 (s, 3H), 3.4–3.5 (m, 2H), 3.55 (dd, J=10.5, 5.2 Hz, 2H), 4.90 (t, J=5.2 Hz, 1H), 6.79 (d, J=7.6 Hz, 1H), 7.28 (dd, J=13.1, 7.6 Hz, 1H), 8.00 (br s, 2H), 8.10 (s, 1H), 8.34 (d, J=1.0 Hz, 1H), 8.58 (d, J=1.0 Hz, 1H), 9.95 (s, 1H), 10.2–10.4 (m, 1H)
FABMS m/z 340 (M+H)$^+$ C$_{17}$H$_{17}$N$_5$O$_3$=339.

EXAMPLE 11

Compound 12

LK6-A (60 mg, 0.19 mmol) was dissolved in dimethyl sulfoxide (4 ml), and 0.32 ml of an aqueous solution of galactosamine hydrochloride (109.2 mg, 0.51 mmol) and potassium carbonate (36 mg, 0.26 mmol) was added thereto, followed by stirring at room temperature for 12 hours. Then, the reaction mixture was poured into water (200 ml) and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (82:18), whereby Compound 12 (47.8 mg, 54%) was obtained.

$^1$H NMR (400 MHz, DMSO-d$_6$) δ [only major component (α-form) is shown] 2.34 (s, 3H), 3.4–3.6 (m, 4H), 3.78 (br s, 1H), 3.88 (t, J=6.4 Hz, 1H), 4.57 (t, J=5.7 Hz, 1H), 4.61 (d, J=4.6 Hz, 1H), 4.91 (d, J=7.3 Hz, 1H), 5.14 (t, J=3.9 Hz, 1H), 6.78 (d, J=7.5 Hz, 1H), 6.82 (d, J=4.6 Hz, 1H), 7.26 (dd, J=12.8, 7.5 Hz, 1H), 7.99 (s, 2H), 8.10 (s, 1H), 8.34 (d, J=1.9 Hz, 1H), 8.57 (d, J=1.9 Hz, 1H), 9.95 (s, 1H), 10.2 (dd, J=12.7, 9.8 Hz, 1H)
FABMS m/z 458 (M+H)$^+$ C$_{21}$H$_{23}$N$_5$O$_7$=457.

EXAMPLE 12

Compound 13

LK6-A (60 mg, 0.19 mmol) was dissolved in dimethyl sulfoxide (4 ml), and 0.32 ml of an aqueous solution of glucosamine hydrochloride (109.2 mg, 0.51 mmol) and potassium carbonate (36 mg, 0.21 mmol) was added thereto, followed by stirring at room temperature for 12 hours. Then, the reaction mixture was poured into water (200 ml), and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (84:16), whereby Compound 13 (47.8 mg, 54%) was obtained.

α-form: β-form=3:1 (signal ratio) α-form: $^1$H NMR (400 MHz, DMSO-d$_6$) δ 2.34 (s, 3H), 3.1–3.2 (m, 2H), 3.4–3.6 (m, 2H), 3.6–3.7 (m, 2H), 4.45 (t, J=5.9 Hz, 1H), 4.97 (d, J=5.6 Hz, 1H), 5.12 (t, J=4.1 Hz, 1H), 5.16 (d, J=6.1 Hz, 1H), 6.79 (d, J=7.6 Hz, 1H), 6.90 (d, J=4.1 Hz, 1H), 7.25 (dd, J=12.9, 7.6 Hz, 1H), 8.01 (br s, 2H), 8.10 (s, 1H), 8.34 (d, J=1.9 Hz, 1H), 8.57 (d, J=1.9 Hz, 1H), 9.90 (s, 1H), 10.2 (dd, J=12.9, 9.5 Hz, 1H) β-form: $^1$H NMR (400 MHz, DMSO-d$_6$) δ 2.34 (s, 3H), 2.88 (dd, J=8.3, 18.1 Hz, 1H), 3.1–3.2 (m, 1H), 3.4–3.6 (m, 2H), 3.7–3.8 (m, 2H), 4.54 (t, J=5.8 Hz, 1H), 4.59 (t, J=7.7 Hz, 1H), 5.05 (d, J=5.4 Hz, 1H), 5.28 (d, J=6.1 Hz, 1H), 6.81 (d, J=8.5 Hz, 1H), 6.93 (d, J=7.7 Hz, 1H), 7.2–7.3 (m, 1H), 8.01 (br s, 2H), 8.10 (s, 1H), 8.34 (d, J=1.9 Hz, 1H), 8.57 (d, J=1.9 Hz, 1H), 9.90 (s, 1H), 10.2–10.3 (m, 1H)
FABMS m/z 458 (M+H)$^+$ C$_{21}$H$_{23}$N$_5$O$_7$=457.

EXAMPLE 13

Compound 14

LK6-A (60 mg, 0.19 mmol) was dissolved in dimethyl sulfoxide (4 ml), and 0.32 ml of an aqueous solution of mannosamine hydrochloride (109.2 mg, 0.51 mmol) and potassium carbonate (36 mg, 0.21 mmol) was added thereto, followed by stirring at room temperature for 12 hours. Then, the reaction mixture was poured into water (300 ml), and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (82:18), whereby Compound 14 (51.0 mg, 57.6%) was obtained.
FABMS m/z 458(M+H)$^+$ C$_2$H$_{23}$ N$_5$O$_7$=457.

EXAMPLE 14

Compound 15

LK6-A (60 mg, 0.19 mmol) was dissolved in dimethyl sulfoxide (4 ml), and 0.32 ml of an aqueous solution of D-glucamine (91.2 mg, 0.50 mmol) was added thereto, followed by stirring at room temperature for 12 hours. Then, the reaction mixture was poured into water (300 ml), and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (82:18), whereby Compound 15 (49.0 mg, 55.0%) was obtained.

$^1$H NMR (400 MHz, DMSO-d$_6$) δ 2.34 (s, 3H), 3.2–3.7 (m, 8H), 4.3–4.5 (m, 4H), 4.97 (d, J=5.1 Hz, 1H), 6.78 (d, J=7.4 Hz, 1H), 7.26 (dd, J=13.0, 7.4 Hz, 1H), 8.01 (br s, 2H), 8.10 (s, 1H), 8.34 (d, J=1.0 Hz, 1H), 8.58 (d, J=1.0 Hz, 1H), 9.97 (s, 1H), 10.3–10.4 (m, 1H)
FABMS m/z 460 (M+H)$^+$ C$_{21}$H$_{25}$N$_5$O$_7$=459.

EXAMPLE 15

Compound 16

LK6-A (60 mg, 0.19 mol) was dissolved in dimethyl sulfoxide (4 ml), and 0.3 ml of an aqueous solution of 1-amino-1-deoxy-β-D-galactose (173.4 mg, 0.97 mmol) was added thereto, followed by stirring at room temperature for 24 hours. Then, the reaction mixture was poured into water (200 ml), and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (84:16), whereby Compound 16 (32.7 mg, 37%) was obtained.

$^1$H NMR (400 MHz, DMSO-d$_6$) δ 2.36 (s, 3H), 3.3–3.6 (m, 5H), 3.6–3.8 (m, 1H), 4.33 (t, J=8.6 Hz, 1H), 4.49 (d, J=5.4 Hz, 1H), 4.63 (t, J=5.4 Hz, 1H), 4.80 (d, J=5.9 Hz, 1H), 5.24 (d, J=5.6 Hz, 1H), 6.94 (d, J=7.8 Hz, 1H), 7.35 (dd, J=12.6, 7.8 Hz, 1H), 8.06 (br s, 2H), 8.12 (s, 1H), 8.35 (d, J=3.4 Hz, 1H), 8.60 (d, J=3.4 Hz, 1H), 9.97 (s, 1H), 10.29 (dd, J=12.6, 8.7 Hz, 1H)
FABMS m/z 458 (M+H)$^+$ C$_{21}$H$_{23}$N$_5$O$_7$=457.

EXAMPLE 16

Compound 17

LK6-A (60 mg, 0.19 mmol) was dissolved in dimethyl sulfoxide (4 ml), and 0.3 ml of an aqueous solution of 1-amino-1-deoxy-β-D-glucose (173.4 mg, 0.97 mmol) was added thereto, followed by stirring at room temperature for 24 hours. Then, the reaction mixture was poured into water (200 ml), and the resulting mixture was allowed to stand at 5° C. for 3 days for precipitation. The precipitate was separated by filtration through a membrane filter and dissolved in dimethyl sulfoxide (1 ml), and chloroform (200 ml) was added thereto. The resulting mixture was purified by silica gel column chromatography with chloroform/methanol (84:16), whereby Compound 17 (27.4 mg, 31%) was obtained.

$^1$H NMR (400 MHz, DMSO-d 6) δ 2.35 (s, 3H), 3.0–3.2 (m, 2H), 3.2–3.3 (m, 1H), 3.4–3.5 (m, 2H), 3.6–3.7 (m, 1H), 4.40 (d, J=8.6 Hz, 1H), 4.57 (d, J=6.0 Hz, 1H), 4.99 (d, J=5.4 Hz, 1H), 5.06 (d, J=4.9 Hz, 1H), 5.41 (d, J=5.6 Hz, 1H), 6.96 (d, J=7.8 Hz, 1H), 7.37 (dd, J=12.3, 7.9 Hz, 1H), 8.07 (br s, 2H), 8.12 (s, 1H), 8.35 (s, 1H), 8.59 (s, 1H), 9.98 (s, 1H), 10.3 (dd, J=12.3, 8.6 Hz, 1H)
FABMS m/z 458 (M+H)$^+$ C$_{21}$H$_{23}$N$_5$O$_7$=457.

EXAMPLE 17

Compound 18

LK6-A (60 mg, 0.19 mmol) was dissolved in dimethyl sulfoxide (3 ml), and 2-acetamido-2-deoxy-1-thio-β-D-glucopyranose-3,4,6-triacetate (80.6 mg, 0.22 mmol) was added thereto, followed by stirring at room temperature for 12 hours. After water (200 ml) was added to the reaction mixture, the product was extracted with chloroform (200 ml). The product was purified by silica gel column chromatography with chloroform/methanol (98:2), whereby Compound 18 (12 mg, 9.2%) was obtained.

$^1$H NMR (400 MHz, DMSO-d$_6$) δ 1.79 (s, 3H), 1.85 (s, 3H), 1.94 (s, 3H), 1.99 (s, 3H), 2.34 (s, 3H), 3.95 (s, 3H), 3.9–4.0 (m, 1H), 4.05 (d, J=9.8 Hz, 1H), 4.09 (dd, J=12.5, 2.2 Hz, 1H), 4.23 (dd, J=12.5, 4.6 Hz, 1H), 4.96 (t, J=9.8 Hz, 1H), 5.21 (t, J=9.8 Hz, 1H), 5.65 (d, J=10.5 Hz, 1H), 7.64 (d, J=12.5 Hz, 1H), 7.89 (d, J=12.5 Hz, 1H), 8.15 (s, 1H), 8.24 (br s, 2H), 8.61 (s, 1H), 10.2 (s, 1H)
FABMS m/z 672 (M+H)$^+$ C$_{30}$H$_{33}$N$_5$O$_{11}$S=671.

EXAMPLE 18

Compound 19

LK6-A (60 mg, 0.19 mmol) was dissolved in dimethyl sulfoxide (4 ml), and 1-thio-β-D-glucose-2,3,4,6-tetraacetate (84.6 mg, 0.23 mmol) was added thereto, followed by stirring at room temperature for 12 hours. After water (200 ml) was added to the reaction mixture, the product was extracted with chloroform (200 ml). The product was purified by silica gel column chromatography with chloroform/methanol (99:1), whereby Compound 19 (8.0 mg, 6.2%) was obtained.

$^1$H NMR (400 MHz, DMSO-d$_6$) δ 1.91 (s, 3H), 1.94 (s, 3H), 1.99 (s, 3H), 2.02 (s, 3H), 2.35 (s, 3H), 3.94 (s, 3H), 4.1–4.3 (m, 3H), 4.9–5.1 (m, 2H), 5.40 (t, J=9.5 Hz, 1H), 5.70 (d, J=10.3 Hz, 1H), 7.63 (d, J=12.5 Hz, 1H), 7.89 (d, J=12.5 Hz, 1H), 8.15 (s, 1H), 8.3–8.4 (m, 2H), 8.63 (s, 1H), 10.2 (s, 1H)
FABMS m/z 673 (M+H)$^+$ C$_{30}$H$_{32}$N$_4$O$_{12}$S=672.

EXAMPLE 19

Compound 20

LK6-A (29.4 mg, 0.09 mmol) was dissolved in dimethyl sulfoxide (6 ml), and ethyl mercaptan (0.050 ml) was added thereto, followed by stirring at room temperature for 20 hours. To the reaction mixture was added water, and the resulting mixture was extracted with chloroform. The organic layer was washed twice with water and then dried over anhydrous sodium sulfate. After the solvent was evaporated under reduced pressure, the residue was purified by silica gel column chromatography with chloroform/methanol (49:1), whereby Compound 20 (23.1 mg, 66%) was obtained.

$^1$H NMR (400 MHz, DMSO-d$_6$) δ 1.41 (t, J=7.4 Hz, 3H), 2.31 (s, 3H), 3.39 (q, J=7.4 Hz, 2H), 3.93 (s, 3H), 7.60 (d, J=12.5 Hz, 1H), 7.79 (br s, 2H), 7.87 (d, J=12.5 Hz, 1H), 8.12 (s, 1H), 8.40 (s, 1H), 10.1 (s, 1H)
FABMS m/z 371 (M+H)$^+$ C$_{18}$H$_{18}$N$_4$O$_3$S=370.

EXAMPLE 20

Compound 21

LK6-A (47.6 mg, 0.15 mmol) was dissolved in dimethyl sulfoxide (10 ml), and benzyl mercaptan (0.10 ml) was added thereto, followed by stirring at room temperature for 48 hours. The reaction mixture was diluted with chloroform, and the resulting diluted solution was passed through a silica gel column for adsorption, followed by elution with chloroform/methanol (9:1). After the eluate was concentrated under reduced pressure, chloroform was added to the residue. The resulting mixture was washed three times with water and the organic layer was dried over anhydrous sodium sulfate. After the solvent was evaporated under reduced pressure, the residue was purified by silica gel column chromatography with chloroform/methanol (24:1), whereby Compound 21 (25.9 mg, 39%) was obtained.

$^1$H NMR (400 MHz, DMSO-d$_6$) δ 2.33 (s, 3H), 3.94 (s, 3H), 4.68 (s, 2H), 7.24 (t, J=7.3 Hz, 1H), 7.31 (t, J=7.3 Hz, 2H), 7.52 (d, J=7.3 Hz, 2H), 7.61 (d, J=12.5 Hz, 1H), 7.87 (d, J=12.5 Hz, 1H), 7.90 (br s, 2H), 8.14 (s, 1H), 8.40 (s, 1H), 10.1 (s, 1H)
FABMS m/z 433 (M+H)$^+$ C$_{23}$H$_{20}$N$_4$O$_3$S=432.

EXAMPLE 21

Compound 22

LK6-A (62 mg, 0.20 mmol) was dissolved in dimethylformamide (6 ml), and N-chlorosuccinimide (40 mg, 0.30 mmol) was added thereto, followed by stirring at room temperature for 2 hours. To the reaction mixture was added water, and the resulting mixture was extracted with ethyl acetate. The organic layer was washed with a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with diisopropyl ether, whereby Compound 22 (8.2 mg, 12%) was obtained.

$^1$H NMR (500 MHz, DMSO-$d_6$) δ 2.35 (s, 3H), 3.95 (s, 3H), 7.63 (d, J=12.5 Hz, 1H), 7.90 (d, J=12.5 Hz, 1H), 8.16 (s, 1H), 8.49 (s, 1H), 10.2 (s, 1H)

FABMS m/z 345 (M+H)$^+$ $C_{16}H_{13}{}^{35}ClN_4O_3$=344.

EXAMPLE 22

Compound 23

The same procedure as in Example 21 was repeated, except that N-bromosuccinimide was used in place of N-chlorosuccinimide, whereby Compound 23 (11 mg, 14%) was obtained.

$^1$H NMR (500 MHz, DMSO-$d_6$) δ 2.35 (s, 3H), 3.95 (s, 3H), 7.63 (d, J=12.5 Hz, 1H), 7.90 (d, J=12.5 Hz, 1H), 8.15 (s, 1H), 8.40 (s, 1H), 10.2 (s, 1H)

FABMS m/z 391, 389 (M+H)$^+$ $C_{16}H_{13}BrN_4O_3$=388.

EXAMPLE 23

Compound 24

The same procedure as in Example 21 was repeated, except that N-iodosuccinimide was used in place of N-chlorosuccinimide, whereby Compound 24 (11 mg, 13%) was obtained.

$^1$H NMR (500 MHz, DMSO-$d_6$) δ 2.34 (s, 3H), 3.95 (s, 3H), 7.63 (d, J=12.5 Hz, 1H), 7.90 (d, J=12.5 Hz, 1H), 8.14 (s, 1H), 8.22 (s, 1H), 10.2 (s, 1H)

FABMS m/z 437 (M+H)$^+$ $C_{16}H_{13}IN_4O_3$=436

EXAMPLE 24

Compound 25

LK6-A (1.55 g, 5.00 mmol) was suspended in chloroform (200 ml), and methanol (40 ml) and potassium carbonate (2.07 g, 15.0 mmol) were added thereto, followed by stirring at room temperature for 24 hours. To the reaction mixture was added water, and the resulting mixture was extracted with chloroform/methanol (9: 1). After the solvent was evaporated under reduced pressure, the residue was purified by silica gel column chromatography with chloroform/methanol (30:1), whereby Compound 25 (1.20 g, 70%) was obtained.

$^1$H NMR (400 MHz, DMSO-$d_6$) δ 2.33 (s, 3H), 3.32 (s, 6H), 3.78 (d, J=5.7 Hz, 2H), 5.05 (t, J=5.7 Hz, 1H), 8.21 (s, 1H), 8.28 (br s, 1H), 8.37 (s, 1H), 8.52 (s, 1H)

FABMS m/z 343 (M+H)$^+$ $C_{17}H_{18}N_4O_4$=342.

EXAMPLE 25

Compound 26

LK6-A (1.00 g, 3.23 mol) was suspended in methanol (90 ml), and a 1 N aqueous solution of sodium hydroxide (20 ml) was added thereto, followed by stirring at room temperature for 2.5 hours. To the reaction mixture was added water, and the resulting mixture was extracted with chloroform. After the solvent-was evaporated under reduced pressure, the residue was purified by silica gel column chromatography with chloroform/methanol (9:1), whereby Compound 26 (359 mg, 37%) was obtained.

$^1$H NMR (400 MHz, DMSO-$d_6$) δ 3.30 (s, 6H), 3.68 (d, J=5.9 Hz, 2H), 5.03 (t, J=5.9 Hz, 1H), 5.94 (s, 1H), 7.10 (br s, 2H), 7.75 (br s, 2H), 8.08 (s, 1H), 8.44 (s, 1H)

FABMS m/z 301 (M+H)$^+$ $C_{15}H_{16}N_4O_3$=300.

EXAMPLE 26

Compound 27

Compound 26 (80 mg, 0.27 mmol) was dissolved in dimethyl sulfoxide (15 ml), and Molecular Sieves 4A (300 mg) was added thereto, followed by stirring at 90–100° C. for 43 hours. To the reaction mixture was added water, and the resulting mixture was extracted with ethyl acetate (400 ml). After the solvent was evaporated under reduced pressure, the residue was purified by silica gel column chromatography with chloroform/methanol (9:1), followed by trituration with isopropyl ether, whereby Compound 27 (34 mg, 47%) was obtained.

$^1$H NMR (400 MHz, DMSO-$d_6$) δ3.90 (s, 3H), 5.93 (s, 1H), 7.18 (br s, 2H), 7.53 (d, J=12.7 Hz, 1H), 7.70 (br s, 2H), 7.82 (d, J=12.7 Hz, 1H), 8.08 (s, 1H), 8.54 (s, 1H)

FABMS m/z 269 (M+H)$^+$ $C_{14}H_{12}N_4O_2$=268.

EXAMPLE 27

Compound 28

Compound 25 (164 mg, 0.48 mmol) was dissolved in chloroform/methanol (9:1, 20 ml), and sodium borohydride (36 mg, 0.96 mmol) was added thereto under ice-cooling, followed by stirring at room temperature for 2 hours. To the reaction mixture was added water, and the resulting mixture was extracted twice with chloroform/methanol (9:1). After the solvent was evaporated under reduced pressure, the residue was purified by silica gel column chromatography with chloroform/methanol (19:1–14:1), followed by trituration with isopropyl ether, whereby Compound 28 (17 mg, 10%) was obtained.

$^1$H NMR (400 MHz, DMSO-$d_6$) δ 1.90 (ddd, J=13.7, 9.5, 3.7 Hz, 1H), 2.14 (ddd, J=13.7, 7.6, 3.7 Hz, 1H), 2.30 (s, 3H), 3.22 (s, 3H), 3.32 (s, 3H), 4.66 (dd, J=7.6, 3.7 Hz, 1H), 4.97 (ddd, J=9.5, 6.1, 3.7 Hz, 1H), 5.58 (d, J=6.4 Hz, 1H),7.66 (br s, 2H), 7.96 (s, 1H), 8.05 (s, 1H), 8.25 (s, 1H), 9.94 (s, 1H)

FABMS m/z 345 (M+H)$^+$ $C_{17}H_{20}N_4O_4$=344.

EXAMPLE 28

Compound 29

Compound 26 (50 mg, 0.17 mmol) was dissolved in chloroform/methanol (9:1, 7 ml), and sodium borohydride (19 mg, 0.50 mmol) was added thereto under ice-cooling, followed by stirring at room temperature for 30 minutes. To the reaction mixture was added water, and the resulting mixture was extracted twice with ethyl acetate. After the solvent was evaporated under reduced pressure, the residue was purified by silica gel column chromatography with chloroform/methanol (9:1), followed by trituration with isopropyl ether, whereby Compound 29 (27 mg, 53%) was obtained.

$^1$H NMR (400 MHz, DMSO-$d_6$) δ 1.87 (ddd, J=13.4, 9.5, 3.9 Hz, 1H), 2.14 (ddd, J=13.4, 7.8, 3.9 Hz, 1H), 3.22 (s, 6H), 4.62 (dd, J=7.8, 3.9 Hz, 1H), 4.90 (ddd, J=9.3, 5.4, 3.9 Hz, 1H), 5.41 (d, J=5.4 Hz, 1H), 5.88 (s, 1H), 6.71 (br s, 2H), 7.24 (br s, 2H), 7.88 (s, 1H), 7.94 (s, 1H)

FABMS m/z 303 (M+H)$^+$ $C_{15}H_{18}N_4O_3$ =302.

EXAMPLE 29

Compound 30

LK6-A (155 mg, 0.500 mmol) was dissolved in chloroform/methanol (9:1, 20 ml), and sodium borohydride (38 mg, 1.0 mmol) was added thereto under ice-cooling, followed by stirring at room temperature for 2 hours. To the reaction mixture was added water, and the resulting mixture was extracted twice with chloroform/methanol (9:1). After the solvent was evaporated under reduced pressure, the residue was purified by silica gel column chromatography with chloroform/methanol (14:1–9:1), followed by trituration with isopropyl ether, whereby Compound 30 (18 mg, 11%) was obtained.

$^1$H NMR (400 MHz, DMSO-$d_6$) δ 1.8–2.0 (m, 1H), 2.1–2.2 (m, 1H), 2.30 (s, 3H), 3.24 (s, 3H), 3.4–3.6 (m, 2H), 4.9–5.1 (m, 1H), 5.53 (d, J=6.1 Hz, 1H), 7.65 (br, 2H), 7.96 (s, 1H), 8.06 (s, 1H), 8.25 (s, 1H), 9.95 (br, 1H)
FABMS m/z 315 (M+H)$^+$ $C_{16}H_{18}N_4O_3$=314.

EXAMPLE 30

Compounds 31 and 32

LK6-A (93 mg, 0.30 mmol) was suspended in chloroform (9 ml), and ethylene glycol (1.5 ml) and potassium carbonate (124 mg, 0.90 ml) were added thereto, followed by stirring at room temperature for 42 hours. To the reaction mixture was added water, and the resulting mixture was extracted with chloroform. The organic layer was washed once with water. After the solvent was evaporated under reduced pressure, the residue was purified by preparative thin layer chromatography with chloroform/methanol (6:1), followed by trituration with isopropyl ether, whereby Compound 31 (6.3 mg, 6.2%) and Compound 32 (8.4 mg, 9.4%) were obtained.

Compound 31: $^1$H NMR(400 MHz, DMSO-$d_6$) δ 2.34 (s, 3H), 3.8–3.9 (m, 2H), 3.83 (d, J=5.4 Hz, 2H), 3.9–4.0 (m, 2H), 5.45 (t, J=5.4 Hz, 1H), 8.14 (s, 1H), 8.29 (br s, 2H), 8.37 (s, 1H1), 8.51 (s, 1H), 10.0 (s, 1H)
FABMS m/z 341 (M+H)$^+$ $C_{17}H_{16}N_4O_4$=340.

Compound 32: $^1$H NMR (400 MHz, DMSO-$d_6$) δ 3.70 (d, J=5.4 Hz, 2H), 3.7–3.9 (m, 2H), 3.9–4.0 (m, 2H), 5.46 (t, J=5.4 Hz, 1H), 5.93 (s, 1H), 7.13 (br s, 2H), 7.77 (br s, 2H), 8.09 (s, 1H), 8.44 (s, 1H)
FABMS m/z 299 (M+H)$^+$ $C_{15}H_{14}N_4O_3$=298.

EXAMPLE 31

Compounds 33 and 34

The same procedure as in Example 30 was repeated, except that propylene glycol was used in place of ethylene glycol, whereby Compound 33 (17 mg, 16%) and Compound 34 (15 mg, 16%) were obtained.

Compound 33: $^1$H NMR (400 MHz, DMSO-$d_6$) δ 1.36 (m, 1H), 1.90 (m, 1H), 2.35 (s, 3H), 3.7–3.8 (m, 2H), 3.75 (d, J=5.4 Hz, 2H), 3.9–4.1 (m, 2H), 5.24 (t, J=5.4 Hz, 1H), 8.13 (s, 1H), 8.28 (br s, 2H), 8.37 (s, 1H), 8.50 (s, 1H), 10.0 (s, 1H)
FABMS m/z 355 (M+H)$^+$ $C_{18}H_{18}N_4O_4$=354.

Compound 34: $^1$H NMR (400 MHz, DMSO-$d_6$) δ 1.34 (m, 1H), 1.88 (m, 1H), 3.63 (d, J=5.4 Hz, 2H), 3.7–3.8 (m, 2H), 3.9–4.0 (m, 2H), 5.21 (t, J=5.4 Hz, 1H), 5.93 (s, 1H), 7.11 (br s, 2H), 7.76 (br s, 2H), 8.08 (s, 1H), 8.43 (s, 1H)
FABMS m/z 313 (M+H)$^+$ $C_{16}H_{16}N_4O_3$=312.

EXAMPLE 32

Compound 35

LK6-A (50 mg, 0.16 mmol) was dissolved in chloroform/methanol (9:1, 7 ml), and triethylamine (0.067 ml, 0.48 mmol) and methyl chloroformate (0.025 ml, 0.32 mmol) were added thereto, followed by stirring at room temperature for 45 minutes. To the reaction mixture was added water, and the resulting mixture was extracted with chloroform/methanol (9:1). After the solvent was evaporated under reduced pressure, the residue was triturated with isopropyl ether, whereby Compound 35 (45 mg, 76%) was obtained.

$^1$H NMR (400 MHz, CDCl$_3$+CD$_3$CO$_2$D) δ 2.37 (s, 3H), 3.90 (s, 3H), 3.92 (s, 3H), 7.10 (d, J=12.5 Hz, 1H), 7.90 (d, J=1.0 Hz, 1H), 7.93 (d, J=12.5 Hz, 1H), 8.18 (s, 1H), 8.38 (s, 1H)
FABMS m/z 369 (M+H)$^+$ $C_{18}H_{16}N_4O_5$=368.

EXAMPLE 33

Compound 36

The same procedure as in Example 32 was repeated, except that ethyl chloroformate was used in place of methyl chloroformate, whereby Compound 36 (64%) was obtained.

$^1$H NMR (400 MHz, CDCl$_3$+CD$_3$CO$_2$D) δ 1.36 (t, J=7.1 Hz, 3H), 2.37 (s, 3H), 3.92 (s, 3H), 4.3–4.4 (m, 2H), 7.11 (d, J=12.5 Hz, 1H), 7.94 (d, J=12.5 Hz, 1H), 7.94 (d, J=1.0 Hz, 1H), 8.17 (d, J=0.7 Hz, 1H), 8.38 (5, 1H)
FABMS m/z 383 (M+H)$^+$ $C_{19}H_{18}N_4O_5$=382.

EXAMPLE 34

Compound 37

The same procedure as in Example 32 was repeated, except that n-propyl chloroformate was used in place of methyl chloroformate, whereby Compound 37 (85%) was obtained.

$^1$H NMR (400 MHz, CDCl$_3$+CD$_3$CO$_2$D) δ 1.01 (t, J=7.5 Hz, 3H), 1.7–1.8 (m, 2H), 2.37 (s, 3H), 3.92 (s, 3H), 4.1–4.3 (m, 2H), 7.11 (d, J=12.5 Hz, 1H), 7.93 (d, J=12.5 Hz, 1H), 7.94 (d, J=1.0 Hz, 1H), 8.18 (s, 1H), 8.38 (s, 1H)
FABMS m/z 313 (M+H)$^+$ $C_{20}H_{20}N_4O_5$=312.

EXAMPLE 35

Compound 38

The same procedure as in Example 32 was repeated, except that n-butyl chloroformate was used in place of methyl chloroformate, whereby Compound 38 (56%) was obtained.

$^1$H NMR (400 MHz, CDCl$_3$+CD$_3$ CO$_2$D) δ 0.93 (t, J=7.3 Hz, 3H), 1.3–1.5 (m, 2H), 1.6–1.8 (m, 2H), 2.35 (s, 3H), 3.91 (s, 3H), 4.12 (t, J=6.7 Hz, 2H), 7.09 (d, J=12.0 Hz, 1H), 7.91 (d, J=1.0 Hz, 1H), 7.92 (d, J=12.2 Hz, 1H), 8.17 (d, J=1.0 Hz, 1H), 8.36 (s, 1H)
FABMS m/z 411 (M+H)$^+$ $C_{21}H_{22}N_4O_5$=410.

EXAMPLE 36

Compound 39

The same procedure as in Example 32 was repeated, except that n-octyl chloroformate was used in place of methyl chloroformate, whereby Compound 39 (79%) was obtained.

$^1$H NMR (400 MHz, CDCl$_3$+CD$_3$CO$_2$D) δ 0.8–1.8 (m, 15H), 2.36 (s, 3H), 3.92 (s, 3H), 4.2–4.4 (m, 2H), 7.11 (d, J=12.5 Hz, 1H), 7.93 (d, J=12.7 Hz, 1H), 7.93 (s, 1H), 8.18 (s, 1H), 8.37 (s, 1H)
FABMS m/z 467 (M+H)$^+$ $C_{25}H_{30}N_4O_4$=466.

EXAMPLE 37

Compound 40

The same procedure as in Example 32 was repeated, except that benzyl chloroformate was used in place of methyl chloroformate, whereby Compound 40 (80%) was obtained.

$^1$H NMR (400 MHz, CDCl$_3$+CD$_3$CO$_2$D) δ 2.36 (s, 3H), 3.91 (s, 3H), 5.17 (s, 2H), 7.10 (d, J=12.5 Hz, 1H), 7.3–7.5 (m, 5H), 7.92 (d, J=12.5 Hz, 1H), 7.94 (d, J=0.7 Hz, 1H), 8.16 (s, 1H), 8.37 (s, 1H)
FABMS m/z 445 (M+H)$^+$ C$_{24}$H$_{20}$N$_4$O$_5$=444.

EXAMPLE 38

Compound 41

Compound 25 (97 mg, 0.28 mmol) was dissolved in dimethylformamide (5 ml), and sodium hydride (57 mg, 1.4 mmol) and iodomethane (0.088 ml, 1.4 mmol) were added thereto under ice-cooling, followed by stirring at room temperature for one hour. To the reaction mixture was added water, and the resulting mixture was extracted with ethyl acetate. After the solvent was evaporated under reduced pressure, the residue was purified by preparative thin layer chromatography with chloroform/methanol (9:1), followed by trituration with isopropyl ether, whereby Compound 41 (26 mg, 23%) was obtained.
$^1$H NMR (400 MHz, CDCl$_3$) δ 1.27 (d, J=7.1 Hz, 3H), 2.00 (s, 3H), 3.30 (s, 3H), 3.39 (s, 3H), 3.51 (s, 3H), 3.68 (br s, 6H), 4.67 (quintet, J=7.1 Hz, 1H), 4.84 (d, J=7.8 Hz, 1H), 7.17 (s, 1H), 8.54 (s, 1H), 8.64 (s, 1H)
FABMS m/z 399 (M+H)$^+$ C$_{21}$H$_{26}$N$_4$O$_4$=398.

EXAMPLE 39

Compounds 42 and 43

Compound 26 (60 mg, 0.20 mmol) was dissolved in dimethylformamide (4 ml) in an atmosphere of argon, and sodium hydride (48 mg, 1.2 mmol) and iodomethane (0.075 ml, 1.2 mmol) were added thereto under ice-cooling, followed by stirring at room temperature for 15 minutes. To the reaction mixture was added water, and the resulting mixture was extracted with ethyl acetate. After the solvent was evaporated under reduced pressure, the residue was purified by preparative thin layer chromatography-with chloroform/methanol (9:1). Then, the obtained two fractions were triturated with isopropyl ether, whereby Compound 42 (32 mg, 35%) and Compound 43 (5.7 mg, 7.7%) were obtained.
Compound 42: $^1$H NMR (400 MHz, CDCl$_3$) δ 1.28 (d, J=7.1 Hz, 3H), 3.33 (s, 3H), 3.43 (s, 3H), 3.62 (s, 6H), 3.65 (br s, 6H), 4.70 (quintet, J=7.1 Hz, 1H), 4.82 (d, J=8.3 Hz, 1H), 5.72 (s, 1H), 8.31 (s, 1H), 8.64 (s, 1H)
FABMS m/z 371 (M+H)$^+$ C$_{20}$H$_{26}$N$_4$O$_3$=370.
Compound 43: $^1$H NMR (400 MHz, CDCl$_3$) δ 3.62 (s, 6H), 3.65 (br s, 6H), 3.85 (s, 3H), 5.77 (s, 1H), 7.27 (d, J=13.2 Hz, 1H), 7.93 (d, J=12.7 Hz, 1H), 8.32 (s, 1H), 8.72 (s, 1H)
FABMS m/z 325 (M+H)$^+$ C$_{18}$H$_{20}$N$_4$O$_2$=324.

EXAMPLE 40

Compound 44

Compound 25 (900 mg, 2.63 mmol) was dissolved in chloroform/methanol (9:1, 100 ml), and triethylamine (0.73 ml, 5.3 mmol) and tetrabutylammonium tribromide (2.04 g, 4.21 mmol) were added thereto, followed by stirring at room temperature for 20 minutes. To the reaction mixture was added water, and the resulting mixture was extracted twice with chloroform/methanol (9:1). The organic layer was washed with a saturated aqueous solution of sodium chloride, and then dried over anhydrous sodium sulfate. After the solvent was evaporated under reduced pressure, the residue was purified by silica gel column chromatography with chloroform/methanol (30:1), whereby Compound 44 (1.02 g, 92%) was obtained.
$^1$H NMR (500 MHz, DMSO-d$_6$) δ 2.34 (s, 3H), 3.32 (s, 6H), 3.79 (d, J=5.6 Hz, 2H), 5.04 (t, J=5.6 Hz, 1H), 8.13 (s, 1H), 8.28 (s, 1H), 10.1 (br s, 1H)
FABMS m/z 423, 421 (M+H)$^+$ C$_{17}$H$_{17}$$^{79}$BrN$_4$O$_4$=420.

EXAMPLE 41

Compound 45

Compound 44 (100 mg, 0.238 mmol) was dissolved in dimethylformamide (10 ml), and diisopropylethylamine (0.21 ml, 1.2 mmol) and dimethylamine hydrochloride (98 mg, 1.2 mmol) were added thereto, followed by stirring at 70° C. for 2.5 hours. To the reaction mixture was added water, and the resulting mixture was extracted twice with ethyl acetate. The organic layer was washed with a saturated aqueous solution of sodium chloride, and then dried over anhydrous sodium sulfate. After the solvent was evaporated under reduced pressure, the residue was purified by silica gel column chromatography with chloroform/methanol (30:1), whereby Compound 45 (27 mg, 29%) was obtained.
$^1$H NMR (400 MHz, CDCl$_3$) δ 2.27 (s, 3H), 3.32 (s, 6H), 3.38 (s, 6H), 3.76 (d, J=5.6 Hz, 2H), 5.07 (t, J=5.6 Hz, 1H), 6.79 (br s, 2H), 8.05 (s, 1H), 8.44 (s, 1H), 9.82 (s, 1H)
FABMS m/z 386 (M+H)$^+$ C$_{19}$H$_{23}$N$_5$O$_4$=385.

EXAMPLE 42

Compound 46

Compound 45 (46 mg, 0.12 mmol) was dissolved in dimethyl sulfoxide (10 ml), and Molecular Sieves 4A (200 mg) was added thereto, followed by stirring at 90° C. for 40 hours. To the reaction mixture was added chloroform (200 ml), and the resulting mixture was passed through a silica gel column for adsorption, followed by elution with chloroform/methanol/triethylamine (190:10:3). The eluate was triturated with isopropyl ether, whereby Compound 46 (14 mg, 33%) was obtained.
$^1$H NMR (400 MHz, DMSO-d$_6$) δ 2.30 (s, 3H), 3.45 (br s, 6H), 3.95 (s, 3H), 6.95 (br s, 2H), 7.60 (d, J=12.7 Hz, 1H), 7.89 (d, J=12.4 Hz, 1H), 8.14 (s, 1H), 8.60 (s, 1H), 10.0 (br s, 1H)
FABMS m/z 354 (M+H)$^+$ C$_{18}$H$_{19}$N$_5$O$_3$=353.

EXAMPLE 43

Compound 47

Compound 44 (150 mg, 0.356 mmol) was dissolved in dimethylformamide (10 ml), and 1-methylpiperazine (0.20 ml, 1.8 mmol) was added thereto, followed by stirring at 70° C. for 6 hours. To the reaction mixture was added water, and the resulting mixture was extracted twice with ethyl acetate. The organic layer was washed with a saturated aqueous solution of sodium chloride, and then dried over anhydrous sodium sulfate. After the solvent was evaporated under reduced pressure, the residue was purified by silica gel column chromatography with chloroform/methanol (9:1), followed by trituration with isopropyl ether, whereby Compound 47 (88 mg, 56%) was obtained.
$^1$H NMR (400 MHz, CDCl$_3$) δ 2.35 (s, 3H), 2.39 (s, 3H), 2.62 (t, J=5.1 Hz, 4H), 3.46 (s, 6H), 3.73 (d, J=5.6 Hz, 2H), 3.94 (t, J=5.1 Hz, 4H), 5.14 (br s, 2H), 5.15 (t, J=5.6 Hz, 1H), 8.15 (s, 1H), 8.56 (s, 1H), 8.94 (br s, 1H)
FABMS m/z 441 (M+H)$^+$ C$_{22}$H$_{28}$N$_6$O$_4$=440.

EXAMPLE 44

Compound 48

The same procedure as in Example 42 was repeated, except that Compound 47 (60 mg, 0.14 mmol) was used in place of Compound 45, whereby Compound 48 (31 mg, 54%) was obtained.

$^1$H NMR (400 MHz, CDCl$_3$) δ 2.36 (s, 3H), 2.39 (s, 3H), 2.62 (t, J=5.1 Hz, 4H), 3.94 (s, 3H), 3.95 (t, J=5.1 Hz, 4H), 5.06 (br s, 2H), 7.23 (d, J=12.5 Hz, 1H), 7.94 (d, J=12.5 Hz, 1H), 8.14 (s, 1H), 8.64 (s, 1H), 8.95 (br s, 1H)
FABMS m/z 409 (M+H)$^+$ C$_{21}$H$_{24}$N$_6$O$_3$=408.

EXAMPLE 45

Compound 49

The same procedure as in Example 43 was repeated, except that morpholine (0.16 ml, 1.8 mmol) was used in place of 1-methylpiperazine, whereby Compound 49 (93 mg, 61%) was obtained from Compound 44 (150 mg, 0.356 mmol).

$^1$H NMR (400 MHz, CDCl$_3$) δ 2.36 (s, 3H), 3.46 (s, 6H), 3.73 (d, J=5.6 Hz, 2H), 3.8–3.9 (m, 8H), 5.13 (br s, 2H), 5.15 (t, J=5.6 Hz, 1H), 8.16 (s, 1H), 8.54 (s, 1H), 8.94 (br s, 1H)
FABMS m/z 428 (M+H)$^+$ C$_{21}$H$_{25}$N$_5$O$_5$=427.

EXAMPLE 46

Compound 50

The same procedure as in Example 42 was repeated, except that Compound 49 (60 mg, 0.14mmol) was used in place of Compound 45, whereby Compound 50 (42 mg, 76%) was obtained.

$^1$H NMR (400 MHz, CDCl$_3$) δ 2.36 (s, 3H), 2.61 (s, 2H), 3.91 (s, 6H), 3.94 (s, 3H), 5.07 (br s, 2H), 7.22 (d, J=12.5 Hz, 1H), 7.94 (d, J=12.5 Hz, 1H), 8.15 (s, 1H), 8.62 (s, 1H), 8.96 (br s, 1H)
FABMS m/z 396 (M+H)$^+$ C$_{20}$H$_{21}$N$_5$O$_4$=395.

EXAMPLE 47

Compound 51

The same procedure as in Example 43 was repeated, except that sodium azide (154 mg, 2.38 mmol) was used in place of 1-methylpiperazine, whereby Compound 51 (104 mg, 76%) was obtained from Compound 44 (200 mg, 0.475 mmol).

$^1$H NMR (400 MHz, DMSO-d$_6$) δ 2.36 (s, 3H), 3.34 (s, 6H), 3.83 (d, J=5.6 Hz, 2H), 5.07 (t, J=5.6 Hz, 1H), 7.98 (br s, 2H), 8.40 (s, 1H), 8.78 (s, 1H), 10.2 (br s, 1H)
FABMS m/z 384 (M+H)$^+$ C$_{17}$H$_{17}$N$_7$O$_4$=383.

EXAMPLE 48

Compound 52

The reaction was carried out in a manner similar to that in Example 42, except that Compound 51 (60 mg, 0.14 mmol) was used in place of Compound 45. The reaction mixture was filtered, followed by addition of water and extraction with ethyl acetate. The organic layer was washed with water and a saturated aqueous solution of sodium chloride, and then dried over anhydrous sodium sulfate. After the solvent was evaporated under reduced pressure, the residue was triturated with isopropyl ether, whereby Compound 52 (12 mg, 21%) was obtained.

$^1$H NMR (400 MHz, DMSO-d$_6$) δ 2.37 (s, 3H), 3.97 (s, 3H), 7.62 (d, J=12.7 Hz, 1H), 7.92 (br s, 2H), 7.94 (d, J=12.5 Hz, 1H), 8.42 (s, 1H), 8.85 (s, 1H), 10.3 (br s, 1H)
FABMS m/z 352 (M+H)$^+$ C$_{16}$H$_{13}$N$_7$O$_3$=351.

EXAMPLE 49

Compound 53

Compound 25 (200 mg, 0.585 mmol) was dissolved in dimethyl sulfoxide (10 ml), and benzylamine (0.64 ml, 59 mmol) was added thereto, followed by stirring at room temperature for 4 days. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (9:1), whereby Compound 53 (214 mg, 81%) was obtained.

$^1$H NMR (300 MHz, CDCl$_3$) δ 2.26 (s, 3H), 3.31 (s, 6H), 3.74 (d, J=5.9 Hz, 2H), 4.75 (d, J=5.4 Hz, 2H), 5.06 (t, J=5.9 Hz, 1H), 6.62 (br s, 2H), 7.26 (t, J=7.3 Hz, 1H), 7.35 (t, J=7.5 Hz, 2H), 7.44 (d, J=7.6 Hz, 2H), 7.99 (s, 1H), 8.37 (br s, 1H), 8.66 (s, 1H), 9.78 (s, 1H)
FABMS m/z 448 (M+H)$^+$ C$_{24}$H$_{25}$N$_5$O$_4$=447.

EXAMPLE 50

Compound 54

The reaction was carried out in a manner similar to that in Example 42, except that Compound 53 (60 mg, 0.14 mmol) was used in place of Compound 45. The reaction mixture was filtered, followed by addition of water and extraction with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with isopropyl ether, whereby Compound 54 (6.1 mg, 33%) was obtained.

$^1$H NMR (300 MHz, DMSO-d$_6$) δ 2.28 (s, 3H), 3.93 (s, 3H), 4.75 (br s, 2H), 6.57 (br s, 2H), 7.27 (t, J=7.6 Hz, 1H), 7.35 (t, J=7.6 Hz, 2H), 7.45 (d, J=7.6 Hz, 2H), 7.61 (d, J=12.7 Hz, 1H), 7.87 (d, J=12.7 Hz, 1H), 8.03 (s, 1H), 8.42 (br s, 1H), 8.78 (s, 1H), 9.92 (s, 1H)
FABMS m/z 416 (M+H)$^+$ C$_{23}$H$_{21}$N$_5$O$_3$=415.

EXAMPLE 51

Compound 55

Compound 25 (50 mg, 0.15 mmol) was dissolved in dimethyl sulfoxide (3 ml), and piperidine (0.14 ml, 1.5 mmol) was added thereto, followed by stirring at room temperature for 20 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (50:1), whereby Compound 55 (53 mg, 83%) was obtained.

$^1$H NMR (300 MHz, CDCl$_3$) δ 1.79 (br s, 6H), 2.36 (s, 3H), 3.46 (s, 6H), 3.73 (d, J=5.7 Hz, 2H), 3.96 (br s, 4H), 5.15 (t, J=5.7 Hz, 1H), 8.18 (s, 1H), 8.61 (br s, 1H), 8.92 (s, 1H)
FABMS m/z 426 (M+H)$^+$ C$_{22}$H$_{27}$N$_5$O$_4$=425.

EXAMPLE 52

Compound 56

The same procedure as in Example 50 was repeated, except that Compound 55 (47 mg, 0.11 mmol) was used in place of Compound 53, whereby Compound 56 (21 mg, 49%) was obtained.

$^1$H NMR (300 MHz, DMSO-d$_6$) δ 1.69 (br s, 6H), 2.29 (s, 3H), 3.84 (br s, 2H), 3.94 (s, 3H), 6.79 (br s, 2H), 7.62 (d, J=12.5 Hz, 1H), 7.88 (d, J=12.5 Hz, 1H), 8.08 (s, 1H), 8.57 (br s, 1H), 9.98 (s, 1H)
FABMS m/z 416 (M+H)$^+$ C$_{23}$H$_{21}$N$_5$O$_3$=415.

EXAMPLE 53

Compound 57

Compound 25 (50 mg, 0.15 mmol) was dissolved in dimethyl sulfoxide (3 ml), and aniline (0.15 ml, 1.5 mmol) was added thereto, followed by stirring at room temperature for 20 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was triturated with isopropyl ether, whereby Compound 57 (44 mg, 68%) was obtained.

$^1$H NMR (300 MHz, DMSO-d$_6$) δ 2.29 (s, 3H), 3.3–3 (s, 6H), 3.78 (d, J=5.9 Hz, 2H), 5.08 (t, J=5.9 Hz, 1H), 6.97 (t, J=7.5 Hz, 1H), 7.06 (br s, 2H), 7.35 (t, J=7.5 Hz, 2H), 8.07 (s, 1H), 8.16 (d, J=8.1 Hz, 2H), 8.90 (s, 1H), 9.90 (s, 1H), 10.2 (s, 1H)
FABMS m/z 434 (M+H)$^+$ C$_{23}$H$_{23}$N$_5$O$_4$=433.

EXAMPLE 54

Compound 58

The same procedure as in Example 50 was repeated, except that Compound 57 (32 mg, 0.074 mmol) was used in place of Compound 53, whereby Compound 58 (7.5 mg, 25%) was obtained.

$^1$H NMR (300 MHz, DMSO-d$_6$) δ 2.30 (s, 3H), 3.95 (s, 3H), 6.79 (t, J=7.3 Hz, 1H), 6.99 (br s, 2H), 7.35 (t, J=8.1 Hz, 2H), 7.66 (d, J=12.5 Hz, 1H), 7.91(d, J=12.5 Hz, 1H), 8.10 (s, 1H), 8.17 (d, J=8.1 Hz, 2H), 9.01 (s, 1H), 10.0 (s, 1H), 10.2 (s, 1H)
FABMS m/z 402 (M+H)$^+$ C$_{22}$H$_{19}$N$_5$O$_3$=401.

EXAMPLE 55

Compound 59

Compound 25 (50 mg, 0.15 mmol) was dissolved in dimethyl sulfoxide (3 ml), and n-butylamine (0.15 ml, 1.5mmol)was added thereto, followed by stirring at room temperature for 20 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 59 (32 mg, 52%) was obtained.

$^1$H NMR (300 MHz, DMSO-d$_6$) δ 0.94 (t, J=7.5 Hz, 3H), 1.43 (sextet, J=7.5 Hz, 2H), 1.66 (quintet, J=7.4 Hz, 2H), 2.05 (s, 3H), 3.30 (s, 6H), 3.50 (br t, 2H), 3.74 (d, J=5.7 Hz, 2H), 5.06 (t, J=5.7 Hz, 1H), 6.65 (br s, 1H), 8.00 (s, 1H), 8.65 (s, 1H), 9.82 (s, 1H)
FABMS m/z 414 (M+H)$^+$ C$_{21}$H$_{27}$N$_5$O$_4$=413.

EXAMPLE 56

Compound 60

The same procedure as in Example 50 was repeated, except that Compound 59 (27 mg, 0.065 mmol) was used in place of Compound 53, whereby Compound 60 (12 mg, 48%) was obtained.

$_1$H NMR (300 MHz, DMSO-d$_6$) δ 0.94 (t, J=7.2 Hz, 3H), 1.43 (sextet, J=7.2 Hz, 2H), 1.67 (quintet, J=7.2 Hz, 2H), 2.28 (s, 3H), 3.50 (t, J=7.2 Hz, 2H), 3.93 (s, 3H), 6.59 (br s, 2H), 7.61 (d, J=12.5 Hz, 1H), 7.88 (d, J=12.5 Hz, 1H), 8.04 (s, 1H), 8.77 (s, 1H), 9.94 (s, 1H)
FABMS m/z 382 (M+H)$^+$ C$_{20}$H$_{23}$N$_5$O$_3$=381.

EXAMPLE 57

Compound 61

Compound 25 (50 mg, 0.15 mmol) was dissolved in dimethyl sulfoxide (3 ml), and propargylamine (0.20 ml, 3.0 mmol) was added thereto, followed by stirring at room temperature for 6 days. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 61 (27 mg, 46%) was obtained.

$^1$H NMR (300 MHz, DMSO-d$_6$) δ 2.26 (s, 3H), 3.21 (t, J=2.6 Hz, 1H), 3.31 (s, 6H), 3.75 (d, J=5.9 Hz, 2H), 4.31 (dd, J=5.3, 2.6 Hz, 2H), 5.05 (t, J=5.8 Hz, 1H), 6.78 (br s, 2H), 8.00 (s, 1H), 8.26 (t, J=5.3 Hz, 1H), 8.62 (s, 1H), 9.82 (s, 1H)
FABMS m/z 396 (M+H)$^+$ C$_{20}$H$_{21}$N$_5$O$_4$=395.

EXAMPLE 58

Compound 62

The same procedure as in Example 50 was repeated, except that Compound 61 (24 mg, 0.061 mmol) was used in place of Compound 53, whereby Compound 62 (3.5 mg, 16%) was obtained.

$^1$H NMR (300 MHz, DMSO-d$_6$) δ 2.28 (s, 3H), 3.21 (s, 1H), 3.93 (s, 3H), 4.31 (br s, 2H), 6.70 (br s, 2H), 7.61 (d, J=12.2 Hz, 1H), 7.87 (d, J=12.1 Hz, 1H), 8.04 (s, 1H), 8.27 (br s, 1H), 8.74 (s, 1H), 9.95 (s, 1H)
FABMS m/z 364 (M+H)$^+$ C$_{19}$H$_{17}$N$_5$O$_3$=363.

EXAMPLE 59

Compound 63

Compound 25 (200 mg, 0.585 mmol) was dissolved in dimethyl sulfoxide (10 ml), and 4-methoxybenzylamine (0.76 ml, 59 mmol) was added thereto, followed by stirring at room temperature for 4 days. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (30:1), whereby Compound 63 (260 mg, 93%) was obtained.

$^1$H NMR (400 MHz, CDCl$_3$) δ 2.35 (s, 3H), 3.44 (s, 6H), 3.71 (d, J=5.6 Hz, 2H), 3.82 (s, 3H), 4.78 (s, 2H), 5.08 (br s, 2H), 5.13 (t, J=5.6 Hz, 1H), 6.91 (d, J=8.9 Hz, 2H), 7.37 (d, J=8.6 Hz, 1H), 8.16 (s, 1H), 8.40 (s, 1H), 8.87 (br s, 1H)
FABMS m/z 478 (M+H)$^+$ C$_{25}$H$_{27}$N$_5$O$_5$=477.

EXAMPLE 60

Compound 64

Compound 63 (44 mg, 0.092 mmol) was dissolved indimethyl sulfoxide (7 ml), and Molecular Sieves 4A (200 mg) was added thereto, followed by stirring at 90° C. for 26 hours. To the reaction mixture was added chloroform (200 ml), and the resulting mixture was passed through a silica gel column for adsorption, followed by elution with chloroform/methanol (30:1). The eluate was purified by preparative thin layer chromatography with chloroform/methanol (9:1), followed by trituration with isopropyl ether, whereby Compound 64 (8.0 mg, 20%) was obtained.

$^1$H NMR (300 MHz, DMSO-d$_6$) δ 2.28 (s, 3H), 3.73 (s, 3H), 3.93 (s, 3H), 4.67 (br s, 2H), 6.58 (br s, 2H), 6.91 (d, J=8.8 Hz, 2H), 7.37 (d, J=8.8 Hz, 2H), 7.61 (d, J=12.7 Hz, 1H), 7.87 (d, J=12.7 Hz, 1H), 8.04 (s, 1H), 8.37 (br s, 1H), 8.77 (s, 1H), 9.93 (s, 1H)
FABMS m/z 446 (M+H)$^+$ C$_{24}$H$_{23}$N$_5$O$_4$=445.

EXAMPLE 61

Compound 65

Compound 25 (50 mg, 0.15 mmol) was dissolved in dimethyl sulfoxide (3ml), and diethylamine (0.31 ml, 3.0mmol) was added thereto, followed by stirring at room temperature for 6 days. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with toluene/ethyl acetate/methanol (5:10:1), whereby Compound 65 (24 mg, 39%) was obtained.

$^1$H NMR (300 MHz, DMSO-d$_6$) δ 1.29 (t, J=7.0 Hz, 6H), 2.27 (s, 3H), 3.32 (s, 6H), 3.7–3.9 (m, 4H), 3.76 (d, J=5.9 Hz, 2H), 5.06 (t, J=5.7 Hz, 1H), 6.72 (br s, 2H), 8.04 (s, 1H), 8.36 (s, 1H), 9.84 (s, 1H)
FABMS m/z 414 (M+H)$^+$ C$_{21}$H$_{27}$N$_5$O$_4$=413.

EXAMPLE 62

Compound 66

Compound 65 (22 mg, 0.053 mmol) was dissolved indimethyl sulfoxide (5 ml), and Molecular Sieves 4A (120 mg) was added thereto, followed by stirring at 90° C. for 24 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 66 (27 mg, 46%) was obtained.

$^1$H NMR (400 MHz, DMSO-d$_6$) δ 1.30 (t, J=7.1 Hz, 6H), 2.28 (s, 3H), 3.81 (q, J=7.1 Hz, 4H), 3.94 (s, 3H), 6.62 (br s, 2H), 7.62 (d, J=12.5 Hz, 1H), 7.87 (d, J=12.7 Hz, 1H), 8.07 (s, 1H), 8.49 (s, 1H), 9.95 (s, 1H)
FABMS m/z 382 (M+H)$^+$ C$_{20}$H$_{23}$N$_5$O$_3$ =381

EXAMPLE 63

Compound 67

Compound 25 (50 mg, 0.15 mmol) was dissolved in dimethyl sulfoxide (3 ml), and pyrrolidine (0.13 ml, 1.5 mmol) was added thereto, followed by stirring at room temperature for 5.5 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was triturated with isopropyl ether, whereby Compound 67 (41 mg, 67%) was obtained.

$^1$H NMR (300 MHz, DMSO-d$_6$) δ 2.0–2.1 (m, 4H), 2.27 (s, 3H), 3.32 (s, 6H), 3.7–3.9 (m, 4H), 3.76 (d, J=5.7 Hz, 2H), 5.07 (t, J=5.9 Hz, 1H), 6.77 (br s, 2H), 8.04 (s, 1H), 8.37 (s, 1H), 9.83 (s, 1H)
FABMS m/z 412 (M+H)$^+$ C$_{21}$H$_{25}$N$_5$O$_4$=411.

EXAMPLE 64

Compound 68

The same procedure as in Example 50 was repeated, except that Compound 67 (32 mg, 0.078 mmol) was used in place of Compound 53, whereby Compound 68 (16 mg, 54%) was obtained.

$^1$H NMR (300 MHz, DMSO-d$_6$) δ 2.0–2.1 (m, 4H), 2.28 (s, 3H), 3.7–3.9 (m, 4H), 3.94 (s, 3H), 6.67 (br s, 2H), 7.62 (d, J=12.7 Hz, 1H), 7.88 (d, J=12.5 Hz, 1H), 8.08 (s, 1H), 8.49 (s, 1H), 9.94 (s, 1H)
FABMS m/z 380 (M+H)$^+$ C$_{20}$H$_{21}$N$_5$O$_3$=379.

EXAMPLE 65

Compound 69

Compound 25 (50 mg, 0.15 mmol) was dissolved in dimethyl sulfoxide (3 ml), and 4-hydroxypiperidine (152 mg, 1.5 mmol) was added thereto, followed by stirring at room temperature for 5.5 hours. To the reaction mixture was added water, and the resulting mixture was extracted with ethyl acetate. The organic layer was washed with water and a saturated aqueous solution of sodium chloride, and then dried over anhydrous sodium sulfate, followed by evaporation of the solvent under reduced pressure, whereby Compound 69 (45 mg, 68%) was obtained.

$^1$H NMR (300 MHz, DMSO-d$_6$) δ 1.4–1.6 (m, 2H), 1.9–2.0 (m, 2H), 2.27 (s, 3H), 3.32 (s, 6H), 3.4–3.5 (m, 2H), 3.7–3.8 (m, 1H), 3.75 (d, J=5.9 Hz, 2H), 4.2–4.3 (m, 2H), 4.77 (d, J=4.4 Hz, 1H), 5.06 (t, J=5.9 Hz, 1H), 6.84 (br s, 2H), 8.03 (s, 1H), 8.46 (s, 1H), 9.82 (s, 1H)
FABMS m/z 442 (M+H)$^+$ C$_{22}$H$_{27}$N$_5$O$_5$=441.

EXAMPLE 66

Compound 70

The same procedure as in Example 50 was repeated, except that Compound 69 (40 mg, 0.091 mmol) was used in place of Compound 53, whereby Compound 70 (20 mg, 54%) was obtained.

¹H NMR (300 MHz, DMSO-d₆) δ 1.4–1.6 (m, 2H), 1.8–2.0 (m, 2H), 2.29 (s, 3H), 3.4–3.6 (m, 2H), 3.7–3.9 (m, 1H), 3.94 (s, 3H), 4.2–4.3 (m, 2H), 4.79 (d, J=4.2 Hz, 1H), 6.79 (br s, 2H), 7.62 (d, J=12.7 Hz, 1H), 7.87 (d, J=12.7 Hz, 1H), 8.07 (s, 1H), 8.57 (s, 1H), 9.97 (s, 1H)
FABMS m/z 410 (M+H)⁺ $C_{21}H_{23}N_5O_4$=409.

EXAMPLE 67

Compound 71

Compound 25 (50 mg, 0.15 mmol) was dissolved in dimethyl sulfoxide (3 ml), and 2-methoxyethylamine (0.13 ml, 1.5 mmol) was added thereto, followed by stirring at room temperature for 6 days. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (19:1), whereby Compound 71 (36 mg, 58%) was obtained.

¹H NMR (300 MHz, DMSO-d₆) δ 2.26 (s, 3H), 3.31 (s, 6H), 3.32 (s, 3H), 3.6–3.7 (m, 4H), 3.73 (d, J=5.7 Hz, 2H), 5.06 (t, J=5.7 Hz, 1H), 6.61 (br s, 2H), 7.99 (s, 1H), 8.04 (br s, 1H), 8.65 (s, 1H), 9.79 (s, 1H)
FABMS m/z 414 (M+H)⁺ $C_{20}H_{25}N_5O_5$=413.

EXAMPLE 68

Compound 72

The reaction was carried out in a manner similar to that in Example 42, except that Compound 71 (34 mg, 0.082 mmol) was used in place of Compound 45. The reaction mixture was filtered, followed by addition of water and extraction with ethyl acetate. The organic layer was washed with water and a saturated aqueous solution of sodium chloride, and then dried over anhydrous sodium sulfate. After the solvent was evaporated under reduced pressure, the residue was triturated with isopropyl ether, whereby Compound 72 (20 mg, 64%) was obtained.

¹H NMR (300 MHz, DMSO-d₆) δ 2.27 (s, 3H), 3.32 (s, 3H), 3.6–3.7 (m, 4H), 3.93 (s, 3H), 6.53 (br s, 2H), 7.60 (d, J=12.5 Hz, 1H), 7.87 (d, J=12.5 Hz, 1H), 8.02 (s, 1H), 8.03 (br s, 1H), 8.76 (s, 1H), 8.91 (s, 1H)
FABMS m/z 384 (M+H)⁺ $C_{19}H_{21}N_5O_4$=383.

EXAMPLE 69

Compound 73

Compound 44 (400 mg, 0.950 mmol) was dissolved in dimethylformamide (10 ml) in an atmosphere of argon, and triethylamine (5 ml), trimethylsilylacetylene (0.67 ml, 4.8 mmol), bis(triphenylphosphine)palladium chloride (67 mg, 0.095 mmol) and copper iodide (36 mg, 0.19 mmol) were added thereto, followed by stirring at 50° C. for one hour. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/acetonitrile (3:1), whereby a trimethylsilylethynylated compound (246 mg, 59%) was obtained. The obtained compound (246 mg, 0.562 mmol) was dissolved in tetrahydrofuran (20 ml), and tetrabutylammonium trifluoride (a 1 M solution in tetrahydrofuran, 0.84 ml) was added thereto, followed by stirring at room temperature for 15 minutes. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by silica gel column chromatography with chloroform/methanol (20:1), followed by trituration with isopropyl ether, whereby Compound 73 (164 mg, 80%) was obtained.

¹H NMR (400 MHz, DMSO-d₆) δ 2.35 (s, 3H), 3.33 (s, 6H), 3.79 (d, J=5.6 Hz, 2H), 4.69 (s, 1H), 5.05 (t, J=5.6 Hz, 1H), 8.15 (s, 1H), 8.39 (s, 1H), 8.63 (br s, 1H), 8.85 (br s, 1H), 10.1 (s, 1H)
FABMS m/z 367 (M+H)⁺ $C_{19}H_{18}N_4O_4$=366.

EXAMPLE 70

Compound 74

The reaction was carried out in a manner similar to that in Example 42, except that Compound 73 (30 mg, 0.082 mmol) was used in place of Compound 45. The reaction mixture was filtered, followed by addition of water. The resulting mixture was extracted three times with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with isopropyl ether, whereby Compound 74 (4.7 mg, 17%) was obtained.

¹H NMR (400 MHz, DMSO-d₆) δ 2.36 (s, 3H), 3.95 (s, 3H), 4.68 (s, 1H), 7.64 (d, J=12.5 Hz, 1H), 7.90 (d, J=12.5 Hz, 1H), 8.17 (s, 1H), 8.51 (s, 1H), 10.2 (br s, 1H)
FABMS m/z 335 (M+H)⁺ $C_{18}H_{14}N_4O_3$=334.

EXAMPLE 71

Compound 75

Compound 73 (70 mg, 0.19 mmol) was dissolved in ethyl acetate (15 ml) in an atmosphere of argon, and palladium/carbon (10%, 35 mg) was added thereto. After the argon was substituted by hydrogen, the reaction mixture was stirred at room temperature for 6 hours. Then, the hydrogen in the reactor was substituted by argon, and the reaction mixture was filtered using Celite. After the solvent was evaporated under reduced pressure, the residue was purified by silica gel column chromatography with chloroform/methanol (50:1), followed by trituration with isopropyl ether, whereby Compound 75 (12 mg, 17%) was obtained.

¹H NMR (400 MHz, CDCl₃) δ 1.49 (t, J=7.6 Hz, 3H), 2.38 (s, 3H), 3.14 (q, J=7.6 Hz, 2H), 3.47 (s, 6H), 3.73 (d, J=5.6 Hz, 2H), 5.16 (t, J=5.6 Hz, 1H), 5.62 (br s, 2H), 8.11 (s, 1H), 8.60 (s, 1H), 9.04 (br s, 1H)
FABMS m/z 371 (M+H)⁺ $C_{19}H_{22}N_4O_4$=370.

EXAMPLE 72

Compound 76

The reaction was carried out in a manner similar to that in Example 42, except that Compound 75 (10 mg, 0.027 mmol) was used in place of Compound 45. There action mixture was filtered, followed by addition of water and extraction with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with isopropyl ether, whereby Compound 76 (3.3 mg, 35%) was obtained.

$^1$H NMR (400 MHz, DMSO-$d_6$) δ 2.37 (s, 3H), 2.69 (s, 3H), 3.95 (s, 3H), 7.63 (d, J=12.5 Hz, 1H), 7.90 (d, J=12.7 Hz, 1H), 8.19 (s, 1H), 8.83 (s, 1H), 9.02 (br s, 1H), 9.17 (br s, 1H), 10.3 (br s, 1H)

FABMS m/z 353 (M+H)$^+$ $C_{18}H_{16}N_4O_4$=352.

EXAMPLE 73

Compound 77

Compound 74 (15 mg, 0.045 mmol) was dissolved in ethyl acetate (20 ml) in an atmosphere of argon, and palladium/carbon (10%, 8 mg) was added thereto. After the argon was substituted by hydrogen, the reaction mixture was stirred at room temperature for 3 days. Then, the hydrogen in the reactor was substituted by argon, and the reaction mixture was filtered using Celite. After the solvent was evaporated under reduced pressure, the residue was purified by preparative thin layer chromatography with chloroform/methanol (9:1), whereby Compound 77 (2.0 mg, 13%) was obtained.

$^1$H NMR (400 MHz, DMSO-$d_6$) δ 1.39 (t, J=7.5 Hz, 3H), 2.33 (s, 3H), 3.10 (q, J=7.5 Hz, 2H), 3.94 (s, 3H), 7.64 (d, J=12.5 Hz, 1H), 7.87 (d, J=12.5 Hz, 1H), 7.88 (br s, 2H), 8.11 (s, 1H), 8.59 (s, 1H), 10.1 (s, 1H)

FABMS m/z 339 (M+H)$^+$ $C_{18}H_{18}N_4O_3$=338.

EXAMPLE 74

Compounds 78 and 79

Compound 26 (51 mg, 0.17 mmol) was dissolved in tetrahydrofuran (7 ml), and N-bromosuccinimide (38 mg, 0.21 mmol) was added thereto under ice-cooling, followed by stirring for 10 minutes. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1) followed by trituration with isopropyl ether, whereby Compound 78 (15 mg, 23%) and Compound 79 (22 mg, 28%) were obtained. Compound 78: $^1$H NMR (400 MHz, CDCl$_3$) δ 3.44 (s, 6H), 3.71 (d, J=5.6 Hz, 2H), 5.15 (t, J=5.6 Hz, 1H), 5.41 (br s, 2H), 5.57 (br s, 2H), 5.87 (s, 1H), 8.54 (s, 1H)

FABMS m/z 381, 379 (M+H)$^+$ $C_{15}H_{15}{}^{79}BrN_4O_3$=378.

Compound 79: $^1$H NMR (400 MHz, CDCl$_3$) δ 3.44 (s, 6H), 3.72 (d, J=5.9 Hz, 2H), 5.15 (t, J=5.9 Hz, 1H), 5.90 (br s, 2H), 6.12 (br s, 2H), 8.56 (s, 1H)

FABMS m/z 461, 459, 457 (M+H)$^+$ $C_{15}H_{14}{}^{79}Br_2N_4O_3$=456.

EXAMPLE 75

Compound 80

Compound 26 (60 mg, 0.17 mmol) was dissolved in 1,4-dioxane (8 ml), and N-bromosuccinimide (50 mg, 0.28 mmol) was added thereto under ice-cooling, followed by stirring at room temperature for 2 hours. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with isopropyl ether, whereby Compound 80 (14 mg, 18%) was obtained.

$^1$H NMR (400 MHz, CDCl$_3$) δ 3.42 (s, 6H), 3.73 (d, J=5.6 Hz, 2H), 5.14 (t, J=5.6 Hz, 1H), 6.27 (br s, 2H), 8.22 (s, 1H), 8.61 (s, 1H)

FABMS m/z 381, 379 (M+H)$^+$ $C_{15}H_{15}{}^{79}BrN_4O_3$=378.

EXAMPLE 76

Compound 81

LK6-A (62 mg, 0.20 mmol) was dissolved in chloroform/methanol (9:1, 10 ml), and N-bromosuccinimide (46 mg, 0.26 mmol) was added thereto, followed by stirring at room temperature for 15 minutes. To the reaction mixture was added water, and the resulting mixture was extracted with chloroform. The organic layer was washed with a saturated aqueous solution of sodium chloride, and then dried over anhydrous sodium sulfate. After the solvent was evaporated under reduced pressure, the residue was purified by preparative thin layer chromatography with chloroform/methanol (9:1), followed by trituration with isopropyl ether, whereby Compound 81 (13 mg, 13%) was obtained.

$^1$H NMR (400 MHz, CDCl$_3$) δ 2.34 (s, 3H), 3.36 (s, 3H), 3.46 (s, 3H), 4.97 (d, J=8.0 Hz, 1H), 6.82 (d, J=8.0 Hz, 1H), 8.19 (s, 1H), 8.36 (s, 1H), 10.3 (br s, 1H)

FABMS m/z 503, 501, 499 (M+H)$^+$ $C_{17}H_{16}{}^{79}Br_2N_4O_4$=498.

EXAMPLE 77

Compound 82

LK6-A (93 mg, 0.30 mmol) was dissolved in chloroform/methanol (6:1, 14 ml), and N-bromosuccinimide (161 mg, 0.90 mmol) was added thereto, followed by stirring at room temperature for 1.5 hours. To the reaction mixture was added water, and the resulting mixture was extracted with chloroform. The organic layer was washed with a saturated aqueous solution of sodium chloride, and then dried over anhydrous sodium sulfate. After the solvent was evaporated under reduced pressure, the residue was purified by silica gel column chromatography with chloroform/methanol (60:1), followed by trituration with isopropyl ether, whereby Compound 82 (81 mg, 47%) was obtained.

$^1$H NMR (400 MHz, DMSO-$d_6$) δ 2.23 (s, 3H), 3.29 (s, 3H), 3.42 (s, 3H), 5.10 (d, J=8.1 Hz, 1H), 6.11 (d, J=8.1 Hz, 1H), 8.39 (s, 1H), 10.3 (s, 1H)

FABMS m/z 583, 581, 579, 577 (M+H)$^+$ $C_{17}H_{15}{}^{79}Br_3N_4O_4$=576.

EXAMPLE 78

Compound 83

Compound 23 (20 mg, 0.050 mmol) was dissolved in dimethylformamide (2 ml), and diisopropylethylamine (0.017 ml, 0.10 mmol) and dimethylamine hydrochloride, (5.0 mg, 0.060 mmol) were added thereto, followed by stirring at room temperature for 2.5 hours. To the reaction mixture was added water, and the resulting mixture was extracted with ethyl acetate. The organic layer was washed with water and a saturated aqueous solution of sodium chloride, and then dried over anhydrous sodium sulfate.

After the solvent was evaporated under reduced pressure, the residue was purified by preparative thin layer chromatography with chloroform/methanol (9:1), followed by trituration with isopropyl ether, whereby Compound 83 (6.2 mg, 31%) was obtained.

$^1$H NMR (400 MHz, CDCl$_3$) δ 2.34 (s, 3H), 3.07 (s, 3H), 3.20 (s, 3H), 6.93 (br d, J=12.0 Hz, 1H), 7.86 (d, J=12.7 Hz, 1H), 8.12 (s, 1H), 8.31 (br s, 2H), 8.41 (s, 1H), 10.1 (s, 1H)
FABMS m/z 404, 402 (M+H)$^+$ C$_{17}$H$_{16}$$^{79}$BrN$_5$O$_2$=401.

EXAMPLE 79

Compound 84

The reaction was carried out in a manner similar to that in Example 42, except that Compound 78 (57 mg, 0.15 mmol) was used in place of Compound 45. The reaction mixture was filtered, followed by addition of water and extraction with ethyl acetate. The organic layer was washed with water and a saturated aqueous solution of sodium chloride, and then dried over anhydrous sodium sulfate. After the solvent was evaporated under reduced pressure, the residue was purified by Florisil chromatography with chloroform/methanol (9:1), followed by trituration with isopropyl ether, whereby Compound 84 (27 mg, 52%) was obtained.

$^1$H NMR (400 MHz, DMSO-d6) δ 3.91 (s, 3H), 5.91 (s, 1H), 7.34 (br s, 2H), 7.51 (d, J=12.5 Hz, 1H), 7.85 (d, J=12.5 Hz, 1H), 7.96 (br s, 2H), 8.32 (s, 1H)
FABMS m/z 349, 347 (M+H)$^+$ C$_{14}$H$_{11}$$^{79}$BrN$_4$O$_2$=346.

EXAMPLE 80

Compound 85

LK6-A (310 mg, 1.00 mmol) was suspended in methanol (80 ml), and a 10 N aqueous solution of sodium hydroxide (2 ml) was added thereto, followed by heating under reflux for 4 hours. After the solvent was evaporated under reduced pressure, water was added to the residue, and the resulting mixture was extracted twice with ethyl acetate. The organic layer was washed with a saturated aqueous solution of sodium chloride, and then dried over anhydrous sodium sulfate. After the solvent was evaporated under reduced pressure, the residue was purified by silica gel column chromatography with chloroform/methanol (9:1), followed by trituration with isopropyl ether, whereby Compound 85 (81 mg, 36%) was obtained.

$^1$H NMR (400 MHz, DMSO-d$_6$) δ 2.80 (s, 3H), 5.94 (s, 1H), 7.06 (br s, 2H), 7.74 (br s, 2H), 8.08 (s, 1H), 8.44 (s, 1H)
FABMS m/z 227 (M+H)$^+$ C$_{12}$H$_{10}$N$_4$O=226.

EXAMPLE 81

Compound 86

Compound 85 (45 mg, 0.20 mmol) and benzaldehyde (0.061 ml, 0.60 mmol) were dissolved in methanol (15 ml), and a 10 N aqueous solution of sodium hydroxide (0.2 ml) was added thereto, followed by stirring at room temperature for 7 days. To the reaction mixture was added water, and the resulting mixture was extracted with ethyl acetate. The organic layer was washed with a saturated aqueous solution of sodium chloride, and then dried over anhydrous sodium sulfate. After the solvent was evaporated under reduced pressure, the residue was purified by preparative thin layer chromatography with chloroform/methanol/aqueous ammonia (9:1:1), followed by trituration with isopropyl ether, whereby Compound 86 (29 mg, 46%) was obtained.

$^1$H NMR (400 MHz, DMSO-d$_6$) δ 5.96 (s, 1H), 7.35 (br s, 2H), 7.4–7.6 (m, 3H), 7.76 (br s, 2H), 7.83 (d, J=16.1 Hz, 1H), 7.9–8.1 (m, 2H), 8.11 (s, 1H), 8.63 (s, 1H), 8.82 (d, J=16.1 Hz, 1H)
FABMS m/z 315 (M+H)$^+$ C$_{19}$H$_{14}$N$_4$O=314.

EXAMPLE 82

Compound 87

The same procedure as in Example 81 was repeated, except that 4-anisaldehyde was used in place of benzaldehyde, whereby Compound 87 (22 mg, 32%) was obtained.

$^1$H NMR (500 MHz, DMSO-d$_6$) δ 3.84 (s, 3H), 5.96 (s, 1H), 7.04 (d, J=8.8 Hz, 2H), 7.33 (br s, 2H), 7.75 (br s, 2H), 7.80 (d, J=16.0 Hz, 1H), 7.96 (d, J=8.8 Hz, 2H), 8.10 (s, 1H), 35 8.61 (s, 1H), 8.69 (d, J=16.0 Hz, 1H)
FABMS m/z 345 (M+H)$^+$ C$_{20}$H$_{16}$N$_4$O$_2$=344.

EXAMPLE 83

Compound 88

The same procedure as in Example 81 was repeated, except that 4-dimethylaminobenzaldehyde was used in place of benzaldehyde, whereby Compound 88 (7.0 mg, 10%) was obtained.

$^1$H NMR (500 MHz, DMSO-d$_6$) δ 3.02 (s, 6H), 5.96 (s, 1H), 6.77 (d, J=8.9 Hz, 2H), 7.31 (br s, 2H), 7.72 (br s, 2H), 7.76 (d, J=15.8 Hz, 1H), 7.82 (d, J=8.9 Hz, 2H), 8.10 (s, 1H), 8.55 (d, J=16.0 Hz, 1H), 8.60 (s, 1H)
FABMS m/z 358 (M+H)$^+$ C$_{21}$H$_{19}$N$_5$O=357.

EXAMPLE 84

Compound 89

The same procedure as in Example 81 was repeated, except that 4-chlorobenzaldehyde was used in place of benzaldehyde, whereby Compound 89 (18 mg, 26%) was obtained.

$^1$H NMR (500 MHz, DMSO-d$_6$) δ 5.96 (s, 1H), 7.38 (br s, 2H), 7.54 (d, J=8.5 Hz, 2H), 7.79 (br s, 2H)., 7.81 (d, J=16.2 Hz, 1H), 8.03 (d, J=8.5 Hz, 2H), 8.11 (s, 1H), 8.63 (s, 1H), 8.83 (d, J=16.1 Hz, 1H)
FABMS m/z 349 (M+H)$^+$ C$_{19}$H$_{13}$$^{35}$ClN$_4$O=348.

EXAMPLE 85

Compound 90

The same procedure as in Example 81 was repeated, except that 4-bromobenzaldehyde was used in place of benzaldehyde, whereby Compound 90 (23 mg, 29%) was obtained.

$^1$H NMR (500 MHz, DMSO-d$_6$) δ 5.96 (s, 1H), 7.39 (br s, 2H), 7.67 (d, J=8.5 Hz, 2H), 7.80 (br s, 2H), 7.80 (d, J=16.0 Hz, 1H), 7.96 (d, J=8.6 Hz, 2H), 8.12 (s, 1H), 8.63 (s, 1H), 8.84 (d, J=16.1 Hz, 1H)
FABMS m/z 395, 393 (M+H)$^+$ C$_{19}$H$_{13}$$^{79}$BrN$_4$O=392.

EXAMPLE 86

Compound 91

The same procedure as in Example 81 was repeated, except that 2-anisaldehyde was used in place of benzaldehyde, whereby Compound 91 (59 mg, 73%) was obtained.

¹H NMR (400 MHz, DMSO-d₆) δ 3.92 (s, 3H), 5.96 (s, 1H), 7.07 (t, J=7.4 Hz, 1H), 7.13 (d, J=8.3 Hz, 1H), 7.29 (br s, 2H), 7.46 (m, 1H), 7.75 (br s, 2H), 8.11 (s, 1H), 8.1–8.2 (m, 1H), 8.22 (d, J=16.1 Hz, 1H), 8.62 (s, 1H), 8.74 (d, J=16.4 Hz, 1H)
FABMS m/z 345 (M+H)⁺ $C_{20}H_{16}N_4O_2$=344.

EXAMPLE 87

Compound 92

The same procedure as in Example 81 was repeated, except that 3-anisaldehyde was used in place of benzaldehyde, whereby Compound 92 (20 mg, 29%) was obtained.

¹H NMR (400 MHz, DMSO-d₆) δ 3.86 (s, 3H), 5.96 (s, 1H), 7.05 (dd, J=8.1, 2.4 Hz, 1H), 7.35 (br s, 2H), 7.40 (t, J=7.8 Hz, 1H), 7.52 (t, J=2.0 Hz, 1H), 7.59 (d, J=7.6 Hz, 1H), 7.76 (br s, 2H), 7.81 (d, J=15.9 Hz, 1H), 8.11 (s, 1H), 8.63 (s, 1H), 8.78 (d, J=15.9 Hz, 1H)
FABMS m/z 345 (M+H)⁺ $C_{20}H_{16}N_4O_2$=344.

EXAMPLE 88

Compound 93

The same procedure as in Example 81 was repeated, except that 3,4-dimethoxybenzaldehyde was used in place of benzaldehyde, whereby Compound 93 (17 mg, 23%) was obtained.

¹H NMR (400 MHz, DMSO-d₆) δ 3.84 (s, 3H), 3.90 (s, 3H), 5.96 (s, 1H), 7.05 (d, J=8.3 Hz, 1H), 7.32 (br s, 2H), 7.53 (dd, J=8.3, 2.0 Hz, 1H), 7.57 (d, J=2.0 Hz, 1H), 7.75 (br s, 2H), 7.80 (d, J=15.9 Hz, 1H), 8.11 (s, 1H), 8.62 (s, 1H), 8.67 (d, J=15.9 Hz, 1H)
FABMS m/z 375 (M+H)⁺ $C_{21}H_{18}N_4O_3$=374.

EXAMPLE 89

Compound 94

The same procedure as in Example 81 was repeated, except that 3,4,5-trimethoxybenzaldehyde was used in place of benzaldehyde, whereby Compound 94 (42 mg, 52%) was obtained.

¹H NMR (400 MHz, DMSO-d₆) δ 3.74 (s, 3H), 3.91 (s, 6H), 5.96 (s, 1H), 7.29 (s, 2H), 7.31 (br s, 2H), 7.76 (br s, 2H), 7.80 (d, J=15.9 Hz, 1H), 8.11 (s, 1H), 8.63 (s, 1H), 8.70 (d, J=15.9 Hz, 1H)
FABMS m/z 405 (M+H)⁺ $C_{22}H_{20}N_4O_4$=404.

EXAMPLE 90

Compound 95

The same procedure as in Example 81 was repeated using Compound 85 (90 mg, 0.40 mmol) and 4-methoxymethoxybenzaldehyde (400 mg, 2.41 mmol), whereby Compound 95 (49 mg, 33%) was obtained.

¹H NMR (400 MHz, DMSO-d₆) δ 3.41 (s, 3H), 5.28 (s, 2H), 5.96 (s, 1H), 7.11 (d, J=8.8 Hz, 2H), 7.33 (br s, 2H), 7.75 (br s, 2H), 7.79 (d, J=16.1 Hz, 1H), 7.95 (d, J=8.8 Hz, 2H), 8.10 (s, 1H), 8.62 (s, 1H), 8.70 (d, J=16.1 Hz, 1H)
FABMS m/z 375 (M+H)⁺ $C_{21}H_{18}N_4O_3$=374.

EXAMPLE 91

Compound 96

Compound 95 (35 mg, 0.094 mmol) was dissolved in tetrahydrofuran (8 ml), and 1 N hydrochloric acid (2 ml) was added thereto, followed by heating under reflux for one hour. To the reaction mixture was added a saturated aqueous solution of sodium hydrogen carbonate, and the resulting mixture was extracted with ethyl acetate. The organic layer was washed with a saturated aqueous solution of sodium chloride, and then dried over anhydrous sodium sulfate. After the solvent was evaporated under reduced pressure, the residue was purified by silica gel column chromatography with chloroform/methanol/aqueous ammonia (9:1:1), whereby Compound 96 (12 mg, 39%) was obtained.

¹H NMR (400 MHz, DMSO-d₆) δ 5.96 (s, 1H), 6.87 (d, J=8.6 Hz, 2H), 7.36 (br s, 2H), 7.76 (d, J=16.1 Hz, 1H), 7.78 (br s, 2H), 7.84 (d, J=8.6 Hz, 2H), 8.12 (s, 1H), 8.61 (d, J=16.1 Hz, 1H), 8.62 (s, 1H), 10.0 (br s, 1H)
FABMS m/z 331 (M+H)⁺ $C_{19}H_{14}N_4O_2$=330.

EXAMPLE 92

Compound 97

The same procedure as in Example 81 was repeated, except that 1-methyl-2-pyrrolecarboxaldehyde was used in place of benzaldehyde, whereby Compound 97 (5.6 mg, 8.8%) was obtained.

¹H NMR (300 MHz, DMSO-d₆) δ 3.80 (s, 3H), 5.95 (s, 1H), 6.1–6.2 (m, 1H), 7.1–7.3 (m, 2H), 7.26 (br s, 2H), 7.73 (br s, 2H), 7.79 (d, J=15.6 Hz, 1H), 8.09 (s, 1H), 8.43 (d, J=15.6 Hz, 1H), 8.60 (s, 1H)
FABMS m/z 318 (M+H)⁺ $C_{18}H_{15}N_5O$=317.

EXAMPLE 93

Compound 98

The same procedure as in Example 81 was repeated, except that 2-thiophenecarboxaldehyde was used in place of benzaldehyde, whereby Compound 98 (12 mg, 19%) was obtained.

¹H NMR (300 MHz, DMSO-d₆) δ 5.96 (s, 1H), 7.22 (dd, J=5.0, 3.7 Hz, 1H), 7.28 (br s, 2H), 7.7–7.9 (m, 4H), 7.97 (d, J=15.8 Hz, 1H), 8.10 (s, 1H), 8.49 (d, J=15.8 Hz, 1H), 8.61 (s, 1H)
FABMS m/z 321 (M+H)⁺ $C_{17}H_{12}N_4OS$=320.

EXAMPLE 94

Compound 99

The same procedure as in Example 81 was repeated, except that 3-thiophenecarboxaldehyde was used in place of benzaldehyde, whereby Compound 99 (7.7 mg, 12%) was obtained.

¹H NMR (300 MHz, DMSO-d₆) δ 5.95 (s, 1H), 7.34 (br s, 2H), 7.69 (ddd, J=5.1, 2.9, 0.6 Hz, 1H), 7.78 (br s, 2H), 7.84 (d, J=16.0 Hz, 1H), 7.92 (dd, J=5.1, 0.7 Hz, 1H), 8.10 (s, 1H), 8.14 (dd, J=2.9, 0.7 Hz, 1H), 8.61 (s, 1H), 8.62 (d, J=16.0 Hz, 1H)
FABMS m/z 321 (M+H)⁺ $C_{17}H_{12}N_4OS$=320.

EXAMPLE 95

Compound 100

The same procedure as in Example 81 was repeated, except that 2-furancarboxaldehyde was used in place of benzaldehyde, whereby Compound 100 (24 mg, 39%) was obtained.

¹H NMR (300 MHz, DMSO-d₆) δ 5.96 (s, 1H), 6.71 (dd, J=3.3, 1.8 Hz, 1H), 7.18 (d, J=3.5 Hz, 1H), 7.21 (br s, 2H), 7.64 (d, J=16.0 Hz, 1H), 7.79 (br s, 2H), 7.92 (d, J=1.7 Hz, 1H), 8.11 (s, 1H), 8.47 (d, J=16.0 Hz, 1H), 8.60 (s, 1H)
FABMS m/z 305 (M+H)$^+$ $C_{17}H_{12}N_4O_2$=304.

EXAMPLE 96

Compound 101

The same procedure as in Example 81 was repeated, except that 3-furancarboxaldehyde was used in place of benzaldehyde, whereby Compound 101 (2.4 mg, 3.9%) was obtained.

$^1$H NMR (300 MHz, DMSO-d$_6$) δ 5.95 (s, 1H), 7.31 (br s, 3H), 7.76 (d, J=15.8 Hz, 1H), 7.78 (br s, 2H), 7.82 (br s, 1H), 8.10 (s, 1H), 8.24 (br s, 1H), 8.53 (d, J=16.0 Hz, 1H), 8.60 (s, 1H)
FABMS m/z 305 (M+H)$^+$ $C_{17}H_{12}N_4O_2$=304;

EXAMPLE 97

Compound 102

The same procedure as in Example 81 was repeated, except that 2-pyridinecarboxaldehyde was used in place of benzaldehyde, whereby Compound 102 (11 mg, 17%) was obtained.

$^1$H NMR (300 MHz, DMSO-d$_6$) δ 5.97 (s, 1H), 7.25 (br s, 2H), 7.44 (ddd, J=7.3, 4.8, 1.1 Hz, 1H), 7.80 (d, J=16.1 Hz, 1H), 7.82 (br s, 2H), 7.92 (td, J=7.7, 1.8 Hz, 1H), 8.12 (s, 1H), 8.16 (d, J=7.7 Hz, 1H), 8.63 (s, 1H), 8.71 (m, 1H), 8.96 (d, J=16.1 Hz, 1H)
FABMS m/z 316 (M+H)$^+$ $C_{18}H_{13}N_5O$=315.

EXAMPLE 98

Compound 103

The same procedure as in Example 81 was repeated, except that 3-pyridinecarboxaldehyde was used in place of benzaldehyde, whereby Compound 103 (11 mg, 17%) was obtained.

$^1$H NMR (300 MHz, DMSO-d$_6$) δ 5.95 (s, 1H), 7.41 (br s, 2H), 7.52 (dd, J=7.9, 4.8 Hz, 1H), 7.81 (br s, 2H), 7.85 (d, J=16.3 Hz, 1H), 8.11 (s, 1H), 8.44 (dt, J=7.9, 1.8 Hz, 1H), 8.6–8.7 (m, 1H), 8.64 (s, 1H), 8.94 (d, J=16.1 Hz, 1H), 9.16 (d, J=1.8 Hz, 1H)
FABMS m/z 316 (M+H)$^+$ $C_{18}H_{13}N_5O$=315.

EXAMPLE 99

Compound 104

The same procedure as in Example 81 was repeated, except that 4-pyridinecarboxaldehyde was used in place of benzaldehyde, whereby Compound 104 (8.3 mg, 20%) was obtained.

$^1$H NMR (300 MHz, DMSO-d$_6$) δ 5.96 (s, 1H), 7.41 (br s, 2H), 7.77 (d, J=16.3 Hz, 1H), 7.89 (br s, 2H), 7.94 (d, J=6.1 Hz, 2H), 8.12 (s, 1H), 8.64 (s, 1H), 8.69 (d, J=6.1 Hz, 2H), 9.01 (d, J=16.1 Hz, 1H)
FABMS m/z 316 (M+H)$^+$ $C_{18}H_{13}N_5O$=315.

EXAMPLE 100

Compound 105

LK6-A (93 mg, 0.30 mmol) was dissolved in dimethyl sulfoxide (10 ml), and piperazine (54 mg, 0.60 mmol) was added thereto, followed by stirring at room temperature for 2 hours. To the reaction mixture was added chloroform (100 ml), and the resulting mixture was passed through a silica gel column for adsorption, followed by elution with chloroform/methanol/aqueous ammonia (9:1:1). The eluate was triturated with isopropyl ether, whereby Compound 105 (95 mg, 87%) was obtained.

$^1$H NMR (300 MHz, DMSO-d$_6$) δ 2.35 (s, 3H), 2.79 (m, 4H), 3.48 (m, 4H), 7.06 (d, J=13.0 Hz, 1H), 7.79 (d, J=12.8 Hz, 1H), 8.00 (br s, 2H), 8.13 (s, 1H), 8.31 (s, 1H), 8.33 (s, 1H), 8.61 (s, 1H), 10.1 (br s, 1H)
FABMS m/z 365 (M+H)$^+$ $C_{19}H_{20}N_6O_2$=364.

EXAMPLE 101

Compound 106

LK6-A (31 mg, 0.10 mmol) was dissolved in dimethyl sulfoxide (3 ml), and 1-acetylpiperazine (64 mg, 0.50 mmol) was added thereto, followed by stirring at room temperature for 5 hours. To the reaction mixture was added water, and the resulting mixture was extracted with chloroform. The organic layer was washed with a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 106 (8.3 mg, 20%) was obtained.

$^1$H NMR (300 MHz, DMSO-d$_6$) δ 2.07 (s, 3H), 2.36 (s, 3H), 3.59 (m, 8H) 7.13 (d, J 13.0 Hz, 1H), 7.85 (d, J=13.0 Hz, 1H), 8.01 (br s, 2H), 8.13 (s, 1H), 8.34 (s, 1H), 8.61 (s, 1H), 10.1 (br s, 1H)
FABMS m/z 407 (M+H)$^+$ $C_2H_{22}N_6O_3$=406.

EXAMPLE 102

Compound 107

Compound 105 (7.2 mg, 0.020 mmol) was dissolved in dimethylformamide (1 ml), and triethylamine (0.0028 ml, 0.020 mmol) and benzoyl chloride (0.0028 ml, 0.024 mmol) were added thereto, followed by stirring at room temperature for 15 minutes. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 107 (2.2 mg, 24%) was obtained.

$^1$H NMR (300 MHz, CDCl 3) δ 2.39 (s, 3H), 3.54 (m, 4H), 3.75 (m, 4H), 6.72 (d, J=12.8 Hz, 1H), 7.26 (m, 2H), 7.60 (m, 1H), 7.95 (d, J=12.8 Hz, 1H), 8.12 (d, J=7.2 Hz, 2H), 8.12 (s, 1H), 8.41 (s, 1H), 8.80 (s, 1H), 9.24 (br s, 1H)
FABMS m/z 469 (M+H)$^+$ $C_{26}H_{24}N_6O_3$=468;

EXAMPLE 103

Compound 108

Compound 105 (6.6 mg, 0.018 mmol) was dissolved in tetrahydrofuran (3 ml), and N-hydroxysuccinidyl 4-azidosalicylate (0.0050 mg, 0.018 mmol) and 4-dimethylaminopyridine (0.0020 ml, 0.016 mmol) were added thereto, followed by stirring at room temperature for 24 minutes. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 108 (4.1 mg, 43%) was obtained.

$^1$H NMR (300 MHz, DMSO-$d_6$) δ 2.34 (s, 3H), 3.3–3.9 (m, 8H), 6.61 (d, J=2.0 Hz, 1H), 6.65 (dd, J=8.1, 2.2 Hz, 1H), 7.14 (br d, J=13.0 Hz, 1H), 7.24 (d, J=8.1 Hz, 1H), 7.84 (br d, J=13.2 Hz, 1H), 8.06 (br s, 2H), 8.13 (s, 1H)., 8.34 (s, 1H), 8.61 (s, 1H), 10.1 (br s, 1H), 10.3 (s, 1H)

FABMS m/z 526 (M+H)$^+$ $C_{26}H_{23}N_6O_4$=525.

EXAMPLE 104

Compound 109

Compound 105 (7.3 mg, 0.020 mmol) was dissolved in dimethylformamide (1 ml), and N-hydroxysuccinidyl 4-azidobenzoate (0.0052 mg, 0.020 mmol) was added thereto, followed by stirring at room temperature for 118 minutes. To the reaction mixture was added water, and the resulting mixture was extracted with ethyl acetate. The organic layer was washed with water and a saturated aqueous solution of sodium chloride, and then dried over anhydrous sodium sulfate. After the solvent was evaporated under reduced pressure, the residue was purified by preparative thin layer chromatography with chloroform/methanol (9:1), whereby Compound 109 (5.2 mg, 51%) was obtained.

$^1$H NMR (300 MHz, CDCl$_3$) δ 2.38 (s, 3H), 3.53 (m, 4H), 3.76 (m, 4H), 5.83 (br s, 2H), 6.74 (d, J=13.0 Hz, 1H), 7.10 (d, J=8.6 Hz, 2H), 7.47 (d, J=8.6 Hz, 2H), 7.92 (d, J=12.8 Hz, 1H), 8.12 (s, 1H), 8.39 (s, 1H), 8.75 (s, 1H), 9.17 (br s, 1H)

FABMS m/z 510 (M+H)$^+$ $C_{26}H_{23}N_9O_3$=509.

EXAMPLE 105

Compound 110

To LK6-A (40.9 mg, 0.13 mmol) was added acetic anhydride (4 ml), followed by stirring at room temperature for 3 hours. To the reaction mixture was added a saturated aqueous solution of sodium hydrogen carbonate, and the resulting mixture was extracted with chloroform. The organic layer was dried over anhydrous sodium sulfate. After the solvent was evaporated under reduced pressure, the residue was purified by silica gel column chromatography with chloroform/methanol (49:1), whereby Compound 110 (30.7 mg, 51%) was obtained.

$^1$H NMR (500 MHz, DMSO-$d_6$) δ 2.10 (s, 3H), 2.16 (s, 3H), 2.30 (s, 3H), 2.41 (s, 3H), 3.96 (s, 3H), 7.53 (d, J=12.5 Hz, 1H), 7.95 (d, J=12.5 Hz, 1H), 8.01 (s, 1H), 8.13 (s, 1H), 9.21 (s, 1H), 10.13 (s, 1H), 10.74 (s, 1H)

FABMS m/z 455 (M+H)$^+$ $C_{22}H_{22}N_4O_7$=454.

EXAMPLE 106

Compound 111

Compound 25 (342 mg, 1.00 mmol) was dissolved in acetic anhydride (20 ml), and the resulting solution was stirred at room temperature for 3 hours. After the acetic anhydride was evaporated under reduced pressure, the residue was purified by silica gel column chromatography with chloroform/methanol (50:1), followed by trituration with isopropyl ether, whereby Compound 111 (166 mg, 34%) was obtained.

$^1$H NMR (400 MHz, CDCl$_3$) δ 2.17 (s, 3H), 2.23 (s, 3H), 2.36 (s, 3H), 2.45 (s, 3H), 3.45 (s, 6H), 3.64 (dd, J=16.0, 5.6 Hz, 1H), 3.69 (dd, J=16.0, 5.6 Hz, 1H), 5.11 (t, J=5.6 Hz, 1H), 7.78 (d, J=1.0 Hz, 1H), 8.17 (d, J=1.0 Hz, 1H), 8.79 (br s, 1H), 9.70 (br s, 1H), 10.9 (br s, 1H)

FABMS m/z 487 (M+H)$^+$ $C_{23}H_{26}N_4O_7$=486.

EXAMPLE 107

Compounds 112 and 113

Compound 111 (70 mg, 0.14 mmol) was dissolved in ethyl acetate/methanol (3:1, 20 ml) in an atmosphere of argon, and palladium/carbon (10%, 30 mg) was added thereto. After the argon was substituted by hydrogen, the reaction mixture was stirred at room temperature for 2.5 hours. Then, the hydrogen in the reactor was substituted by argon, and the reaction mixture was filtered using Celite. After the solvent was evaporated under reduced pressure, the residue was purified by preparative thin layer chromatography with chloroform/methanol (9:1), followed by trituration with isopropyl ether, whereby Compound 112 (19 mg, 32%) and Compound 113 (23 mg, 32%) were obtained.

Compound 112: $^1$H NMR (400 MHz, CDCl$_3$) δ 2.22 (s, 3H), 2.36 (s, 3H), 2.45 (s, 3H), 3.45 (s, 6H), 3.67 (d, J=5.6 Hz, 2H), 5.09 (t, J=5.6 Hz, 1H), 5.36 (d, J=1.2 Hz, 2H), 7.93 (t, J=1.2 Hz, 1H), 9.62 (s, 1H)

FABMS m/z 429 (M+H)$^+$ $C_{21}H_{24}N_4O_5$=428.

Compound 113: $^1$H NMR (400 MHz, CDCl$_3$) δ 2.0–2.1 (m, 1H), 2.1–2.2 (m, 1H), 2.19 (s, 3H), 2.31 (s, 3H), 2.41 (s, 3H), 3.42 (s, 3H), 3.44 (s, 3H), 4.27 (br s, 1H), 4.70 (t, J=5.4 Hz, 1H), 5.03 (dd, J=9.5, 2.9 Hz, 1H), 5.25 (s, 2H), 7.28 (s, 1H), 8.60 (s, 1H), 9.51 (br s, 1H), 11.3 (br s, 1H)

FABMS m/z 431 (M+H)$^+$ $C_{21}H_{26}N_4O_5$=430.

EXAMPLE 108

Compound 114

Compound 110 (60 mg, 0.13 mmol) was dissolved in ethyl acetate/methanol (9:1, 20 ml) in an atmosphere of argon, and palladium/carbon (10%, 30 mg) was added thereto. After the argon was substituted by hydrogen, the reaction mixture was stirred at room temperature for 12 hours. Then, the hydrogen in the reactor was substituted by argon, and the reaction mixture was filtered using Celite. After the solvent was evaporated under reduced pressure, the residue was purified by preparative thin layer chromatography with chloroform/methanol (9:1), followed by trituration with isopropyl ether, whereby Compound 114 (22 mg, 43%) was obtained.

$^1$H NMR (400 MHz, CDCl$_3$+CD$_3$OD) δ 2.21 (s, 3H), 2.35 (s, 3H), 2.44 (s, 3H), 3.42 (s, 3H), 3.58 (t, J=6.2 Hz, 2H), 3.89 (t, J=6.2 Hz, 2H), 5.32 (d, J=1.5 Hz, 2H), 7.88 (s, 1H), 9.60 (s, 1H)

FABMS m/z 399 (M+H)$^+$ $C_{20}H_{22}N_4O_5$=398.

What is claimed is:

1. A compound represented by formula (I):

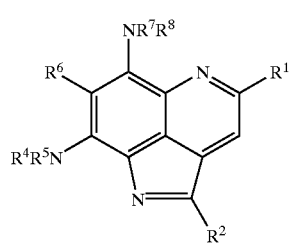

wherein $R^1$ represents lower alkyl (optionally substituted by one or more substituents independently selected from the group consisting of lower alkyl, hydroxy, lower alkoxy and halogen), lower alkanoyl (the lower alkyl moiety being optionally substituted by one or more substituents independently selected from the group consisting of lower alkyl, hydroxy, lower alkoxy and halogen), carboxy, lower alkoxycarbonyl,

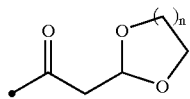

(wherein n represents 1 or 2) or COCH=CHR$^9$ {wherein R$^9$ represents substituted or unsubstituted lower alkoxy, substituted or unsubstituted aryl, substituted or unsubstituted heteroaryl or NR$^{10}$R$^{11}$ (wherein R$^{10}$ and R$^{11}$ independently represent hydrogen, substituted or unsubstituted lower alkyl, substituted or unsubstituted lower alkenyl, substituted or unsubstituted lower alkynyl, substituted or unsubstituted aralkyl, substituted or unsubstituted aryl, substituted or unsubstituted heteroaryl, substituted or unsubstituted heteroaryl-substituted lower alkyl, substituted or unsubstituted tetrahydropyranyl, or substituted or unsubstituted tetrahydropyranylmethyl, or R$^{10}$ and R$^{11}$ are combined together with the adjoining N to form a substituted or unsubstituted heterocyclic group)};

R$^2$ represents NR$^{13}$R$^{14}$ (wherein R$^{13}$ and R$^{14}$ have the same significances as R$^{10}$ and R$^{11}$, respectively);

R$^4$ and R$^5$ independently represent hydrogen, substituted or unsubstituted lower alkyl, substituted or unsubstituted lower alkanoyl, substituted or unsubstituted lower alkoxycarbonyl, substituted or unsubstituted aralkyloxycarbonyl, or substituted or unsubstituted heteroaryl-substituted lower alkoxycarbonyl;

R$^6$ represents hydrogen or halogen; and

R$^7$ and R$^8$ independently represent hydrogen, substituted or unsubstituted lower alkyl, or substituted or unsubstituted lower alkanoyl;

or a pharmaceutically acceptable salt thereof.

2. The compound or the pharmaceutically acceptable salt thereof according to claim 1, wherein R$^1$ represents COCH=CHR$^9$;

R$^4$, R$^5$ and R$^6$ represent hydrogen; and

R$^7$ and R$^8$ independently represent hydrogen or acetyl.

3. The compound or the pharmaceutically acceptable salt thereof according to claim 1, wherein R$^1$ represents said optionally substituted lower alkyl or said optionally substituted lower alkanoyl;

R$^4$, R$^5$ and R$^6$ represent hydrogen; and

R$^7$ and R$^8$ independently represent hydrogen or acetyl.

4. The compound or the pharmaceutically acceptable salt thereof according to claim 1, wherein R$^1$ represents:

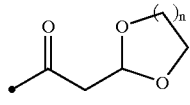

wherein R$^4$, R$^5$ and R$^6$ represent hydrogen; and

R$^7$ and R$^8$ independently represent hydrogen or acetyl.

5. The compound or the pharmaceutically acceptable salt thereof according to claim 1, wherein R$^1$ represents (E)-3-methoxyacryloyl;

R$^4$ represents hydrogen; and

R$^5$ represents substituted or unsubstituted lower alkoxycarbonyl or substituted or unsubstituted aralkyloxycarbonyl.

6. The compound or the pharmaceutically acceptable salt thereof according to claim 1, wherein R$^1$ represents COCHR$^{15}$CH (OCH$_3$)$_2$ (wherein R$^{15}$ represents hydrogen or lower alkyl);

R$^4$ and R$^5$ independently represent hydrogen or lower alkyl; and

R$^7$ and R$^8$ independently represent hydrogen, substituted or unsubstituted lower alkyl or acetyl.

7. The compound or the pharmaceutically acceptable salt thereof according to claim 1, wherein R$^1$ represents COCHR$^{15a}$CH (OCH$_3$)$_2$ (wherein R$^{15a}$ represents hydrogen or halogen);

R$^4$ and R$^5$ represent hydrogen; and

R$^7$ and R$^8$ independently represent hydrogen or acetyl.

8. The compound or the pharmaceutically acceptable salt thereof according to claim 1, wherein R$^1$ represents 1-hydroxy-3-methoxypropyl;

R$^4$ and R$^5$ represent hydrogen; and

R$^7$ and R$^8$ independently represent hydrogen or acetyl.

9. The compound or the pharmaceutically acceptable salt thereof according to claim 1, wherein R$^4$ represents hydrogen;

R$^5$ represents substituted or unsubstituted lower alkanoyl;

R$^7$ represents hydrogen; and

R$^8$ represents acetyl.

10. A pharmaceutical composition comprising at least one of the compounds or the pharmaceutically acceptable salts thereof according to any of claims 1–9 and a pharmaceutically acceptable carrier.

11. A method for immunosuppression which comprises the steps of:

selecting at least one of the compounds or the pharmaceutically acceptable salts thereof according to any of claims 1–9, and administering said compound or salt to a patient in need thereof.

12. The compound or the pharmaceutically acceptable salt thereof according to claim 1, wherein R$^1$ represents (E)-3-methoxyacryloyl.

13. The compound or the pharmaceutically acceptable salt thereof according to claim 12, wherein R$^4$ and R$^5$ represent hydrogen; and R$^7$ and R$^8$ independently represent hydrogen or acetyl.

14. The compound or the pharmaceutically acceptable salt thereof according to claim 12 or 13, wherein R$^{13}$ represents hydrogen; and R$^{14}$ represents substituted or unsubstituted lower alkyl, substituted or unsubstituted lower alkynyl or substituted or unsubstituted aryl.

15. A pharmaceutical composition comprising at least one of the compounds or the pharmaceutically acceptable salts thereof according to claim 12 or 13 and a pharmaceutically acceptable carrier.

16. A pharmaceutical composition comprising at least one of the compounds or the pharmaceutically acceptable salts thereof according to claim 14 and a pharmaceutically acceptable carrier.

17. A method for immunosuppression which comprises the steps of:

selecting at least one of the compounds or the pharmaceutically acceptable salts thereof according to any of claim 12 or 13, and administering said compound or salt to a patient in need thereof.

18. A method for immunosuppression which comprises the steps of:

selecting at least one of the compounds or the pharmaceutically acceptable salts thereof according to claim 14, and administering said compound or salt to a patient in need thereof.

* * * * *